United States Patent
Aramaki et al.

(10) Patent No.: US 12,383,271 B2
(45) Date of Patent: Aug. 12, 2025

(54) MEDICAL DEVICE

(71) Applicant: TERUMO KABUSHIKI KAISHA, Tokyo (JP)

(72) Inventors: Naoki Aramaki, Kanagawa (JP); Miho Kai, Kanagawa (JP); Anri Fujii, Kanagawa (JP); Kensuke Uchitomi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 804 days.

(21) Appl. No.: 17/449,147

(22) Filed: Sep. 28, 2021

(65) Prior Publication Data

US 2022/0008074 A1 Jan. 13, 2022

Related U.S. Application Data

(63) Continuation of application No. PCT/JP2020/014286, filed on Mar. 27, 2020.

(30) Foreign Application Priority Data

Mar. 28, 2019 (JP) .................................. 2019-065048

(51) Int. Cl.
A61B 17/11 (2006.01)
A61B 17/00 (2006.01)

(52) U.S. Cl.
CPC ...... *A61B 17/1114* (2013.01); *A61B 17/0057* (2013.01); *A61B 2017/00004* (2013.01);
(Continued)

(58) Field of Classification Search
CPC ............ A61B 17/0057; A61B 17/1114; A61B 2017/00004; A61B 2017/00592;
(Continued)

(56) References Cited

U.S. PATENT DOCUMENTS 5,176,703 A 1/1993 Peterson
5,534,010 A 7/1996 Peterson
(Continued)

FOREIGN PATENT DOCUMENTS

CN 1390111 A 1/2003
CN 101040785 A 9/2007
(Continued)

OTHER PUBLICATIONS

English Translations of the International Search Report (Form PCT/ISA/210) and the Written Opinion of the International Searching Authority (Form PCT/ISA/237) issued Jun. 23, 2020, by the Japanese Patent Office in corresponding International Application No. PCT/JP2020/014286. (7 pages).
(Continued)

*Primary Examiner* — Mohamed G Gabr
(74) *Attorney, Agent, or Firm* — Buchanan Ingersoll & Rooney PC

(57) ABSTRACT

A medical device is disclosed capable of reducing risk factors of an anastomotic leakage after a surgical operation is performed. The medical device includes an adhesion promotion sheet configured to include an adhesion promotion portion promoting adhesion of biological tissues and a frame portion provided outside the adhesion promotion portion in a plane direction and a pulling unit connected to the adhesion promotion sheet and configured to deform a second region so as to cover at least a portion of an outer peripheral surface of a biological organ to be joined with a pulling operation.

9 Claims, 15 Drawing Sheets

(52) U.S. Cl.
CPC .............. *A61B 2017/00592* (2013.01); *A61B 2017/00623* (2013.01); *A61B 2017/0065* (2013.01); *A61B 2017/00654* (2013.01)

(58) Field of Classification Search
CPC .. A61B 2017/00623; A61B 2017/0065; A61B 2017/00654; A61B 2017/00884; A61B 2017/1135
See application file for complete search history.

(56) References Cited

U.S. PATENT DOCUMENTS

| | | | |
|---|---|---|---|
| 6,458,079 | B1 | 10/2002 | Cohn et al. |
| 8,052,699 | B1 | 11/2011 | Sherwinter |
| 2002/0022861 | A1 | 2/2002 | Jacobs et al. |
| 2002/0173804 | A1* | 11/2002 | Rousseau .......... A61B 17/00234 606/151 |
| 2005/0059996 | A1 | 3/2005 | Bauman et al. |
| 2006/0085030 | A1 | 4/2006 | Bettuchi et al. |
| 2006/0212050 | A1 | 9/2006 | D'Agostino et al. |
| 2007/0049930 | A1 | 3/2007 | Hearn et al. |
| 2009/0299388 | A1 | 12/2009 | Barker et al. |
| 2010/0012703 | A1 | 1/2010 | Calabrese et al. |
| 2011/0278346 | A1 | 11/2011 | Hull et al. |
| 2012/0016410 | A1 | 1/2012 | Belson et al. |
| 2012/0035629 | A1 | 2/2012 | Sherwinter |
| 2012/0310227 | A1 | 12/2012 | Katou |
| 2013/0153634 | A1* | 6/2013 | Carter ................ A61B 17/1155 227/176.1 |
| 2014/0128819 | A1 | 5/2014 | Eaves |
| 2014/0379026 | A1 | 12/2014 | Carrison et al. |
| 2015/0142023 | A1 | 5/2015 | Tannhauser et al. |
| 2015/0257866 | A1 | 9/2015 | Filipiak et al. |
| 2016/0051252 | A1 | 2/2016 | Smith et al. |
| 2018/0214201 | A1 | 8/2018 | Bargon et al. |
| 2019/0282235 | A1* | 9/2019 | Aramaki ............ A61B 17/0469 |

FOREIGN PATENT DOCUMENTS

| | | |
|---|---|---|
| CN | 101296664 A | 10/2008 |
| CN | 102791212 A | 11/2012 |
| CN | 203234772 U | 10/2013 |
| CN | 103533900 A | 1/2014 |
| CN | 105407814 A | 3/2016 |
| CN | 106659561 A | 5/2017 |
| CN | 107072661 A | 8/2017 |
| CN | 112638287 A | 4/2021 |
| EP | 3 845 148 A1 | 7/2021 |
| JP | 2003-533326 A | 11/2003 |
| JP | 2006-255411 A | 9/2006 |
| JP | 3867150 B1 | 1/2007 |
| JP | 2007505708 A | 3/2007 |
| JP | 2008-516669 A | 5/2008 |
| JP | 2009508610 A | 3/2009 |
| JP | 2011-015966 A | 1/2011 |
| JP | 2011-183091 A | 9/2011 |
| JP | 2013-525070 A | 6/2013 |
| JP | 2013-526342 A | 6/2013 |
| JP | 2013123643 A | 6/2013 |
| JP | 2016-540615 A | 12/2016 |
| WO | 2011/139912 A1 | 11/2011 |
| WO | 2014/049676 A1 | 4/2014 |

OTHER PUBLICATIONS

Office Action (Notice of Reasons for Refusal) issued Jul. 4, 2023, by the Japan Patent Office in corresponding Japanese Patent Application No. 2021-509677 and an English translation of the Office Action. (12 pages).

The extended European Search Report issued Apr. 4, 2022, by the European Patent Office in corresponding European Patent Application No. 20779614.5-1122. (8 pages).

Office Action (The First Office Action) issued May 30, 2022, by the State Intellectual Property Office of People's Republic of China in corresponding Chinese Patent Application No. 202080024622.1 and an English Translation of the Office Action. (16 pages).

International Search Report (PCT/ISA/210) with English translation mailed on Jun. 23, 2020, by the Japanese Patent Office as the International Searching Authority for International Application No. PCT/JP2020/014286.

\* cited by examiner

MEDICAL DEVICE

CROSS-REFERENCES TO RELATED APPLICATIONS

This application is a continuation of International Application No. PCT/JP2020/014286 filed on Mar. 27, 2020, which claims priority to Japanese Patent Application No. 2019-065048 filed on Mar. 28, 2019, the entire content of both of which is incorporated herein by reference.

FIELD OF THE DISCLOSURE

The present disclosure generally relates to a medical device.

BACKGROUND DISCUSSION

In the medical field, a medical procedure (for example, anastomosis for a digestive tract) of joining biological organs to each other by performing a surgical operation is known. In a case where the medical procedure as described above is performed, as a prognosis determinant after surgery, it is important that there is no delay in adhesion in a joint portion joined between the biological organs.

In the medical procedure of joining the biological organs, various methods and various medical instruments are used. For example, a method of suturing the biological organs by using a biodegradable suture, or a method of using a mechanical joint device (refer to Japanese Patent Application Publication No. 2007-505708 A) for performing anastomosis by using a stapler has been proposed. In particular, in a case where anastomosis is performed using the mechanical joint device, compared to a method of using the suture, a joining force between the biological organs can be improved in the joint portion. Accordingly, risk factors of an anastomotic leakage can be reduced.

However, a degree of progress of adhesion in the joint portion depends on a state of biological tissues in a joint object site (joint target site) of a patient. Therefore, for example, even in a case where the joint device as disclosed in Japanese Patent Application Publication No. 2007-505708 A is used, depending on the state of the biological tissues of the patient, there is a possibility that the risk factors of the anastomotic leakage cannot be sufficiently reduced.

SUMMARY

A medical device is disclosed, which is capable of reducing risk factors of an anastomotic leakage after a surgical operation is performed.

A medical device is disclosed, which includes an adhesion promotion sheet configured to include a first region promoting adhesion of biological tissues and a second region provided outside the first region in a plane direction and a pulling unit connected to the adhesion promotion sheet and configured to deform the second region so as to cover at least a portion of an outer peripheral surface of a biological organ to be joined with a pulling operation.

According to the medical device according to the present disclosure, the adhesion of the biological tissues of the biological organs can be promoted by interposing the adhesion promotion sheet between the joint target sites of the biological organs to be joined. In addition, the operator can deform the second region of the adhesion promotion sheet so as to cover at least a portion of the outer peripheral surface of the biological organs to be joined by pulling the pulling unit. As a result, the operator can stably hold the adhesion promotion sheet in the biological organs, and can help prevent the adhesion promotion sheet from being distorted or misaligned during the medical procedure. Therefore, the risk of anastomotic leakage of the biological organs can be effectively reduced.

A medical device is disclosed that promotes adhesion between biological tissue, the medical device comprising: an adhesion promotion sheet made of a biodegradable sheet that promotes adhesion of the biological tissue, the adhesion promotion sheet including a first region having a plurality of through-holes that pass through the first region and a second region provided outside the first region in a plane direction; a pulling unit connected to the adhesion promotion sheet and configured to deform the second region so as to cover at least a portion of an outer peripheral surface of a biological organ to be joined with a pulling operation; and wherein the pulling unit includes a connection section connected to the second region and a non-connection section, the non-connection section is not connected to the second region and is configured to be pulled out of the adhesion promotion sheet.

A method is disclosed of promoting adhesion between biological tissue comprising: disposing a medical device at one joint target site, the medical device comprising an adhesion promotion sheet including a first region that promotes adhesion of biological tissues and a second region provided outside the first region in a plane direction, and a pulling unit connected to the adhesion promotion sheet; pulling the pulling unit to deform the adhesion promotion sheet of the medical device to deform the second region; fixing the adhesion promotion sheet of the medical device to the one joint target site; and joining the one joint target site and an other joint target site in a state where at least a portion of the adhesion promotion sheet is disposed between the one joint target site and the other joint target site.

DETAILED DESCRIPTION

Figure 1A:
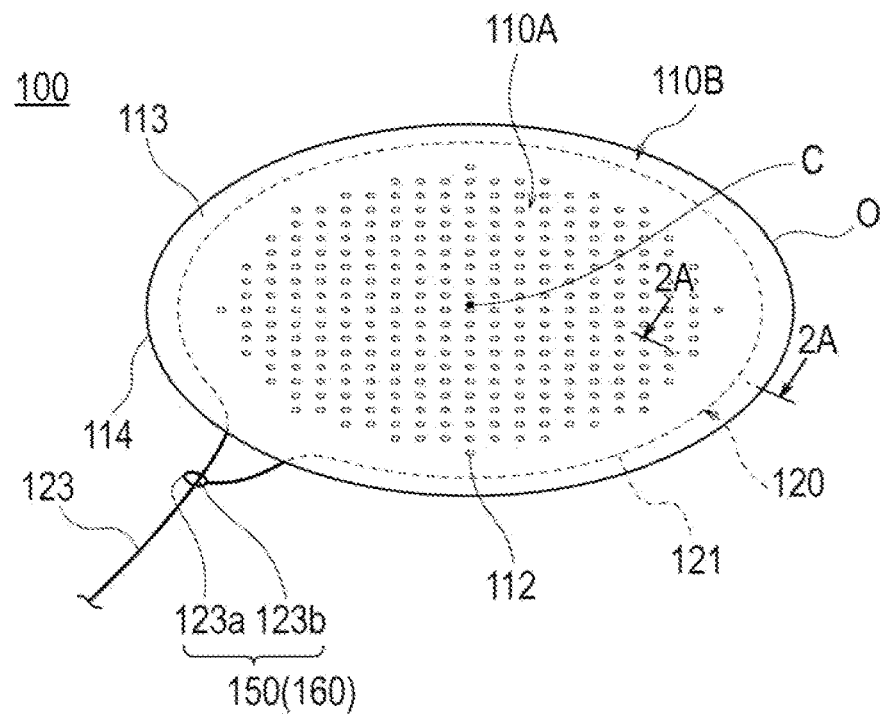
FIG. 1A is a perspective view illustrating a form of a medical device of the present invention.

Set forth below with reference to the accompanying drawings is a detailed description of embodiments of a medical device representing examples of the inventive medical device disclosed here. In the description of the drawings, the same elements are designated by the same reference numerals, and duplicate description will be omitted. In addition, dimensional proportions in the drawings are exaggerated and different from actual proportions for convenience of description, in some cases.

Figure 1B:
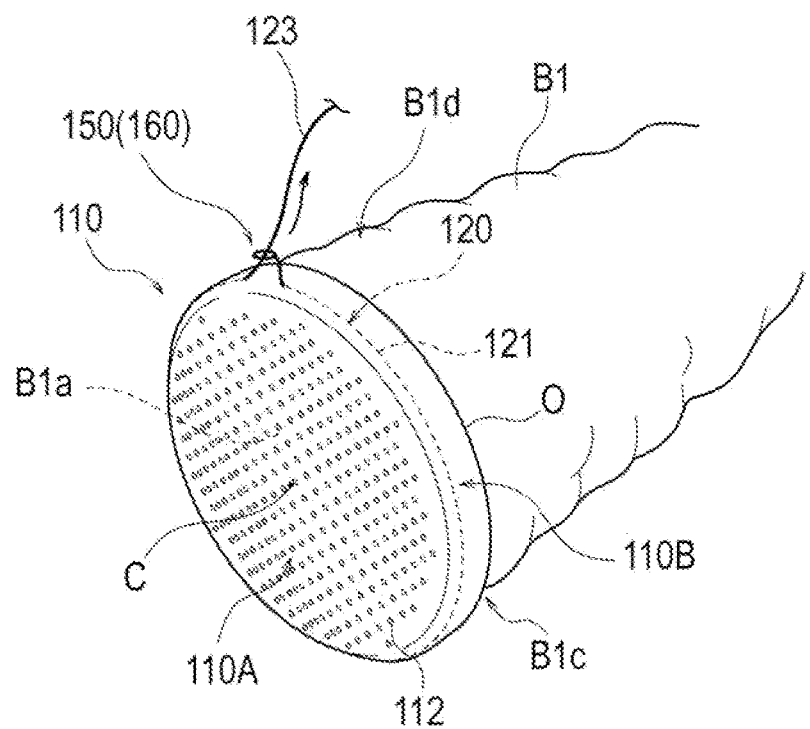
FIG. 1B is a perspective view illustrating a usage example of the medical device in FIG. 1A.
Figure 2:
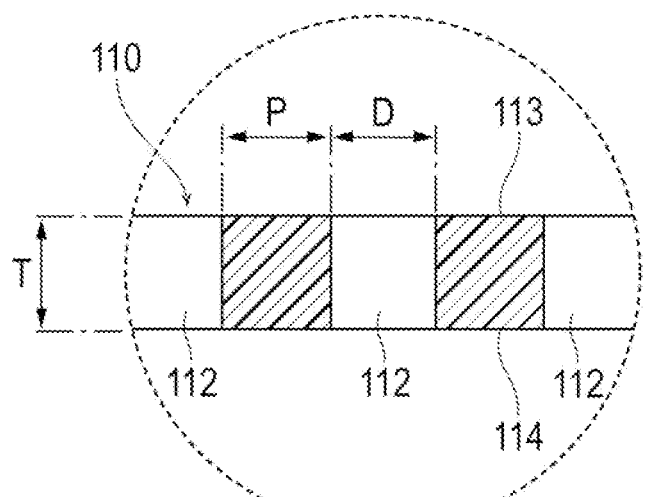
FIG. 2 is an enlarged cross-sectional view illustrating a portion of a cross section taken along line 2A-2A in FIG. 1A.
Figure 3A:
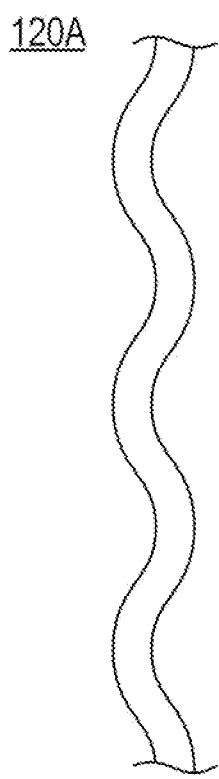
FIGS. 3A-3C are plan views illustrating a shape example of a pulling unit including a string-shaped member.
Figure 3B:
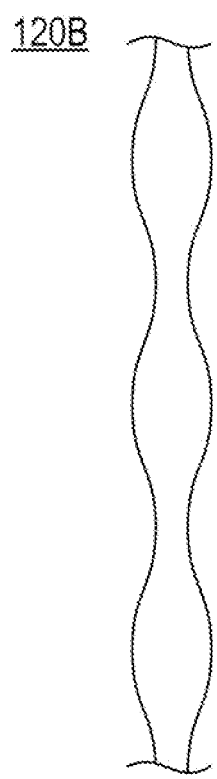
Figure 3C:
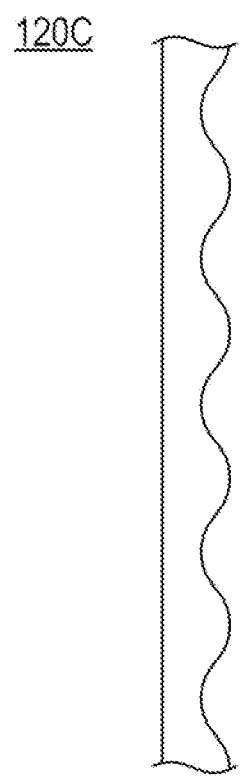

FIG. 1A is a perspective view illustrating a form of a medical device 100. FIG. 1B is a perspective view illustrating a usage example of the medical device 100 in FIG. 1A. FIG. 2 is an enlarged cross-sectional view illustrating a portion of the cross section taken along line 2A-2A in FIG. 1A. FIGS. 3A to 3C are plan views illustrating a shape example of a pulling unit 120.

Medical Device 100

As illustrated in FIG. 1A, the medical device 100 includes an adhesion promotion sheet 110 disposed between biological organs to be joined, and the pulling unit 120 provided on the adhesion promotion sheet 110.

As illustrated in FIGS. 9 to 16, the medical device 100 can be applied to a medical procedure of joining predetermined biological organs (for example, anastomosis for a digestive tract). As will be described later, in the description of the present specification, pancreatic parenchyma-jejunum anastomosis will be described as an example of the medical procedure using the medical device 100.

Adhesion Promotion Sheet 110

As illustrated in FIG. 1A, the adhesion promotion sheet 110 includes an adhesion promotion portion (corresponding to a "first region") 110A that promotes adhesion of biological tissues formed from a biodegradable sheet having a plurality of through-holes 112. The adhesion promotion portion 110A is formed in a predetermined range including a central portion C in a plane direction of the adhesion promotion sheet 110.

The adhesion promotion sheet 110 has a frame portion (corresponding to a "second region") 110B provided more outside (i.e., peripherally of) the adhesion promotion sheet 110 in the plane direction than the adhesion promotion portion 110A. The frame portion 110B is formed in a certain range including an outer peripheral edge O of the adhesion promotion sheet 110 so as to surround the periphery of the adhesion promotion portion 110A. In the present embodiment, the through-hole 112 is not formed in the frame portion 110B.

Adhesion Promotion Portion 110A

As illustrated in FIG. 1A, the through-holes 112 formed in the adhesion promotion portion 110A can be regularly and periodically provided in the plane direction of the adhesion promotion sheet 110. However, each through-hole 112 may be randomly provided at each portion in the plane direction of the adhesion promotion sheet 110.

As illustrated in FIG. 2, each through-hole 112 extends substantially vertically between a front surface 113 and a rear surface (i.e., back surface) 114 along the thickness direction of the adhesion promotion sheet 110 (vertical direction in FIG. 2). Each through-hole 112 may be bent or curved, for example, in a zigzag shape between the front surface 113 and the rear surface 114 in a cross section along the thickness direction of the adhesion promotion sheet 110.

In accordance with an exemplary embodiment, each through-hole 112 has a substantially circular planar shape (shape when the front surface 113 of the adhesion promotion sheet 110 or the rear surface 114 of the adhesion promotion sheet 110 is viewed in a plan view). However, the planar shape of each through-hole 112 is not particularly limited, and may be, for example, an ellipse or a polygon (for example, a rectangle or a triangle). In addition, the plane shape and the cross-sectional shape may be different for each through-hole 112.

In accordance with an exemplary embodiment, the adhesion promotion sheet 110 has a substantially circular planar shape. However, the planar shape of the adhesion promotion sheet 110 is not particularly limited, and may be, for example, an ellipse or a polygon (for example, a rectangle or a triangle).

The thickness of the adhesion promotion sheet 110 (dimension T illustrated in FIG. 2) is not particularly limited, and the thickness of the adhesion promotion sheet 110 can be 0.05 mm to 0.3 mm, preferably 0.1 mm to 0.2 mm. In a case where the thickness of the adhesion promotion sheet 110 is 0.05 mm or more (particularly, for example, in a case of 0.1 mm or more), the adhesion promotion portion 110A can be provided with such strength that the adhesion promotion portion 110A is not damaged when the adhesion promotion sheet 110 is handled. In a case where the thickness of the adhesion promotion sheet 110 is 0.3 mm or less (particularly, for example, in a case of 0.2 mm or less), the adhesion promotion portion 110A can be in close contact with the biological tissue to which the adhesion promotion sheet 110 is applied and can be provided with sufficient flexibility to follow the biological tissue.

In the adhesion promotion portion 110A, a ratio value of the hole diameter D (distance D illustrated in FIG. 2) of the through-hole 112 to the pitch P (distance P illustrated in FIG. 2 and the distance between the through-holes 112 adjacent to each other) of the through-hole 112 is preferably 0.25 or more and less than 40. In a case where the planar shape of the through-hole 112 is a perfect circle, the hole diameter D of the through-hole 112 is equal to the diameter of the perfect circle. In a case where the planar shape of the through-hole 112 is not a perfect circle, the diameter of a perfect circle (equivalent circle diameter) having the same area as an area of an opening portion of the through-hole 112 (portion of the through-hole 112 facing the front surface 113 or the rear surface 114) can be defined as the hole diameter D of the through-hole 112.

Since the adhesion promotion portion 110A includes a plurality of through-holes 112, there are a plurality of values of the hole diameter D corresponding to each through-hole 112. Therefore, in the present embodiment, in calculating the above-described ratio value, an arithmetic average value of two or more values of the hole diameter D corresponding to each of the plurality of through-holes 112 is used as a representative value of the hole diameter D. The pitch P of the plurality of through-holes 112 means a shortest distance between the opening portions of the two through-holes 112. However, with regard to the value of the pitch P, there are a plurality of values of the pitch P corresponding to a combination of the through-holes 112 adjacent to each other. Therefore, according to the present embodiment, in calculating the above-described ratio value, the arithmetic average value of two or more values of the pitch P corresponding to each combination of the through-holes 112 adjacent to each other is used as a representative value of the pitch P.

The pitch P of the above-described through-holes 112, the hole diameter D, and the ratio of the hole diameter D to the pitch P are merely examples, and the present disclosure is not limited to the examples of the pitch P of the through-holes 112, the hole diameter D, and the ratio of the hole diameter D to the pitch P as disclosed.

The adhesion promotion portion 110A can be made of a biodegradable material. The constituent material of the adhesion promotion portion 110A is not particularly limited, and examples of the material of the adhesion promotion portion 110A can include a biodegradable resin. As the biodegradable resin, for example, it is possible to use a known biodegradable (co)polymer such as those disclosed in Japanese Patent Application Publication No. 2011-528275 A, Japanese Patent Application Publication No. 2008-514719 A, Pamphlet of International Publication No. 2008-1952 (i.e., WO 2008/001952), and Japanese Patent Application Publication No. 2004-509205 A. Specifically, the biodegradable resin can include (1) a polymer selected from a group formed of aliphatic polyester, polyester, polyanhydride, polyorthoester, polycarbonate, polyphosphazene, polyphosphate ester, polyvinyl alcohol, polypeptide, polysaccharide, protein, and cellulose; or (2) copolymer formed of one or more monomers forming the above-described materials (1). That is, it is preferable that the biodegradable sheet includes at least one biodegradable resin selected from a group formed of the polymer selected from a group formed of aliphatic polyester, polyester, polyanhydride, polyorthoester, polycarbonate, polyphosphazene, polyphosphate ester, polyvinyl alcohol, polypeptide, polysaccharide, protein, and cellulose, and the copolymer formed of one or more monomers forming the polymer.

A manufacturing method of the adhesion promotion portion 110A is not particularly limited. For example, the manufacturing method includes a method of preparing a fiber formed of the above-described biodegradable resin and manufacturing a mesh-shaped sheet by using the fiber. A method of preparing the fiber formed of the biodegradable resin is not particularly limited. For example, the method can include an electrospinning method (electric field spinning method and electrostatic spinning method) or a melt blowing method. For the method for the adhesion promotion portion 110A, only one of the above-described methods may be selected and used. Alternatively, two or more methods may be selected in appropriate combination with each other for preparing the adhesion promotion 110A. As still another example of the manufacturing method of the adhesion promotion portion 110A, a fiber formed of the above-described biodegradable resin may be spun in accordance with a usual method, and the obtained fiber may be knitted into a mesh shape to manufacture the biodegradable sheet according to the present disclosure.

The adhesion promotion portion 110A causes a biological reaction by using the constituent materials such as the biodegradable resin constituting the adhesion promotion portion 110A. Due to this action, the adhesion promotion portion 110A induces expression of biological components such as fibrin. The biological components induced in this manner can promote adhesion by accumulating in the spaces of the through-holes 112 of the adhesion promotion portion 110A. Therefore, the adhesion promotion portion 110A is disposed between the biological organs to be joined, thereby promoting the adhesion by using the above-described mechanism.

The material of the adhesion promotion portion 110A may not be biodegradable as long as it is possible to promote the adhesion of the biological organs. In addition, the adhesion promotion portion 110A may not have the through-hole 112 regardless of the material, as long as it is possible to promote the adhesion of the biological organs.

Frame Portion 110B

As illustrated in FIG. 1A, the frame portion 110B is formed on the adhesion promotion sheet 110 so as to surround the periphery of the adhesion promotion portion 110A. The frame portion 110B is preferably formed to have a higher rigidity (i.e., greater rigidity) than that of the adhesion promotion portion 110A so that the frame portion 110B is not easily deformed when an external force is applied. The frame portion 110B can be made of, for example, a biodegradable sheet in which a hole portion such as a through-hole 112 is not formed, a resin sheet having a higher rigidity than that of the adhesion promotion portion 110A, or a non-woven fabric.

In addition, the through-hole 112 is not formed in a certain region including the outer peripheral edge O of the biodegradable sheet which is a constituent material of the adhesion promotion portion 110A, so that the adhesion promotion sheet 110 may be provided with the frame portion 110B. In addition, after forming the through-hole 112 in a certain region including the outer peripheral edge O of the biodegradable sheet which is a constituent material of the adhesion promotion portion 110A, only the region is compressed or heated in the thickness direction to crush the through-hole 112. Accordingly, a portion in which the constituent materials of the biodegradable sheet are densely assembled may be formed, and the portion may be used as the frame portion 110B.

In addition, the frame portion 110B may be provided with a suppressing portion that suppresses a synechia with the biological organs at least in a part of the frame portion 110B. The material constituting the suppressing portion of the frame portion 110B is not particularly limited as long as it is possible to suppress the synechia with the biological organs. For example, the suppressing portion of the frame portion 110B may be a non-woven fabric. In addition, the suppressing portion of the frame portion 110B can be made of a biodegradable material, similarly to the adhesion promotion portion 110A.

The area ratio of the adhesion promotion portion 110A and the frame portion 110B in the adhesion promotion sheet 110, the shapes of the adhesion promotion portion 110A and the frame portion 110B in a plan view, and the like are not particularly limited.

Pulling Unit 120

As illustrated in FIGS. 1A and 1B, the medical device 100 can include the pulling unit 120 that is connected to the adhesion promotion sheet 110 and deforms the frame portion 110B so as to cover at least a portion of the outer peripheral surface of the pancreatic parenchyma B1 to be joined with the pulling operation.

The pulling unit 120 can include a string-shaped member having a predetermined length. The pulling unit 120 includes a connection section 121 connected to the frame portion 110B and a non-connection section 123 that is not connected to the frame portion 110B and that can be pulled by an operator and extends outside of the frame portion 110b of the adhesion promotion sheet 110.

The connection section 121 of the pulling unit 120 is inserted through the inside of the adhesion promotion sheet 110. Inside the adhesion promotion sheet 110, a space (not illustrated) into which the connection section 121 is slidably inserted is formed. In the present embodiment, as illustrated in FIG. 1B, the pulling unit 120 is disposed on the adhesion promotion sheet 110 so that the frame portion 110B of the adhesion promotion sheet 110 constitutes an opening portion of a bag (drawstring bag) having a space inside when the non-connection section 123 is pulled in the adhesion promotion sheet 110. In accordance with an exemplary embodiment, the operator can adjust the opening area of the opening portion of the bag configured to include the adhesion promotion sheet 110 by adjusting the pulling amount of the non-connection section 123 of the pulling unit 120.

The method of attaching the pulling unit 120 to the adhesion promotion sheet 110 is not particularly limited. In addition, the pulling unit 120 may be configured so as to be separated from the adhesion promotion sheet 110, or may be configured so as to be retrofitted with a member separate from the adhesion promotion sheet 110.

In accordance with an exemplary embodiment, the pulling unit 120 is disposed in the frame portion 110B with a length equal to or more than half the adhesion promotion sheet 110 along the circumferential direction. In the present embodiment, as illustrated in FIG. 1B, the connection section 121 is disposed at a corresponding portion on a posterior wall B1c (portion of the pancreatic parenchyma B1 on a dorsal side in the circumferential direction) side of the pancreatic parenchyma B1. The non-connection section 123 can be disposed at a corresponding portion of an anterior wall B1d (portion of the pancreatic parenchyma B1 on a ventral side in the circumferential direction) of the pancreatic parenchyma B1 of the adhesion promotion sheet 110. However, the position where the connection section 121 of the pulling unit 120 is disposed on the adhesion promotion sheet 110 is not particularly limited.

The medical device 100 can include an adjustment unit 150 that can adjust the amount of deformation of the frame portion 110B by limiting the pulling operation of the pulling unit 120. In the present embodiment, the adjustment unit 150 is configured to include an annular portion 123a which is a portion of the non-connection section 123 and an insertion portion 123b through which the annular portion 123a is inserted. The pulling operation of the pulling unit 120 can be restricted by adding, for example, an uneven shape, a notch, or the like (for example, structures illustrated in FIGS. 3A-4G) to a portion of the non-connection section 123 and hooking the non-connection section 123 on the annular portion 123a to fit the non-connection section 123. In addition, by configuring the adjustment unit 150 as described above, the adjustment unit 150 also has a function as a lock mechanism 160 that automatically maintains a pulled state without maintaining the state where the operator pulls the pulling unit 120 with fingers or the like. The adjustment unit 150 and the lock mechanism 160 may include, for example, a fixing member made of a member separated from the pulling unit 120. In addition, the non-connection section 123 may be configured so that at least a part of the non-connection section 123 cannot pass through the annular portion 123a.

For example, the pulling unit 120 can be made of a thermoplastic elastomer such as vinyl chloride, polyurethane elastomer, polystyrene elastomer, styrene-ethylene-butylene-styrene copolymer (SEBS), and styrene-ethylene-propylene-styrene copolymer (SEPS), a thermoplastic resin such as nylon and PET, or rubber, silicone elastomer, fiber material, and metals such as SUS wire (i.e., stainless steel wire), copper wire, titanium wire, and nitinol wire. In addition, the pulling unit 120 may be made of, for example, the same material as that of the adhesion promotion portion 110A. By using the same material as that of the adhesion promotion portion 110A, it is possible to manufacture at the same manufacturing site as that of the adhesion promotion portion 110A, so that the manufacturing work is rather easy.

FIGS. 3A and 3B illustrate an example of the shape of the pulling unit 120. As illustrated in FIG. 3A, for example, a pulling unit 120A can include a string-shaped member having a wavy outer shape. In addition, as illustrated in FIG. 3B, for example, a pulling unit 120B can include a string-shaped member having a bump-like outer shape (shape in which a projection portion and a recessed portion are alternately formed along the extending direction). In addition, as illustrated in FIG. 3C, a pulling unit 120C can include a string-shaped member having an outer shape in which one end side intersecting the extending direction is formed in a straight line and the other end side is formed in a wavy shape. For example, the pulling unit 120A and the pulling unit 120B are formed of an elastic material, so that the pulling unit 120A and the pulling unit 120B can be deformed in a straight line when the pulling operation is performed, and the pulling unit 120A and the pulling unit 120B can be configured to return to the original shape when the pulling operation is released. With this configuration, when each of the pulling units 120A and 120B is pulled, the friction between each of the pulling units 120A and 120B and the adhesion promotion sheet 110 can be reduced, and the adhesion promotion sheet 110 can be prevented from being damaged. In addition, in the pulling unit 120C illustrated in FIG. 3C, one end side intersecting the extending direction is formed in a straight line, so that the friction with the adhesion promotion sheet 110 can be further reduced.

As will be described later, a pulling unit 220 can also be configured to include a strip-shaped member (for example, as illustrated in FIGS. 4A-4G). In the present specification, the strip-shaped member can be defined as a member having a larger cross-sectional area than that of the string-shaped member. As an example of the strip-shaped member, a member having a long side and a short side formed in a cross-sectional shape can be cited, and the cross-sectional shape is not limited to the strip-shaped member.

FIG. 1B illustrates a state when the adhesion promotion sheet 110 is disposed on the pancreatic parenchyma Ba. The operator disposes the adhesion promotion portion 110A of the adhesion promotion sheet 110 so as to overlap a cut surface B1a of the pancreatic parenchyma Ba. At this time, the operator disposes the non-connection section 123 of the pulling unit 120 on the anterior wall B1d (portion of the pancreatic parenchyma B1 on the ventral side in the circumferential direction) side of the pancreatic parenchyma B1. The operator deforms the frame portion 110B by pulling the pulling unit 120 on the anterior wall B1d side of the pancreatic parenchyma B1 in a direction separated from the pancreatic parenchyma B1. When the pulling unit 120 is pulled, the adhesion promotion sheet 110 is deformed into a bag shape so as to cover a portion of the outer peripheral surface of the pancreatic parenchyma B1. When the operator pulls the pulling unit 120 by a predetermined length, the subsequent pulling operation is limited by the adjustment unit 150. As a result, it possible to prevent the pancreatic parenchyma B1 from being excessively tightened by the pulling unit 120. By deforming the adhesion promotion sheet 110 so as to cover the pancreatic parenchyma B1, the adhesion promotion sheet 110 can be stably held by the pancreatic parenchyma B1.

As described above, the medical device 100 according to the present embodiment includes the adhesion promotion sheet 110 provided with the adhesion promotion portion 110A promoting adhesion of the biological tissues formed of the biodegradable sheet having the plurality of through-holes 112, and the frame portion 110B provided outside the adhesion promotion portion 110A in the plane direction, and the pulling unit 120 that is connected to the adhesion promotion sheet 110 and deforms the frame portion 110B so as to cover at least a portion of the outer peripheral surface of the biological organ to be joined with the pulling operation.

According to the medical device 100 configured as described above, the adhesion of the biological tissues of the biological organs can be promoted by interposing the adhesion promotion sheet 110 between the joint target sites of the biological organs to be joined. In addition, the operator can deform the frame portion 110B of the adhesion promotion sheet 110 so as to cover at least a portion of the outer peripheral surface of the biological organs to be joined by pulling the pulling unit 120. As a result, the operator can stably hold the adhesion promotion sheet 110 in the biological organs, and can help prevent the adhesion promotion sheet 110 from being distorted or misaligned during the medical procedure. Therefore, the risk of anastomotic leakage of the biological organs can be effectively reduced.

In addition, the pulling unit 120 can include the connection section 121 connected to the frame portion 110B, and the non-connection section 123 that is not connected to the frame portion 110B and is pulled out of the adhesion promotion sheet 110. Therefore, the operator can deform the frame portion 110B so as to cover the outer peripheral surface of the biological organ by a simple operation of pulling the non-connection section 123.

In addition, the connection section 121 is connected to the frame portion 110B with a length equal to or more than half the adhesion promotion sheet 110 along the circumferential direction. Therefore, the operator can more reliably deform the adhesion promotion sheet 110 into a desired shape by pulling the pulling unit 120.

In addition, the pulling unit 120 can include a string-shaped member having a predetermined length. Therefore, the operator can rather easily deform the adhesion promotion sheet 110 into a desired shape by pulling the pulling unit 120.

In addition, the medical device 100 can include the adjustment unit 150 that can adjust the amount of deformation of the frame portion 110B by limiting the pulling operation of the pulling unit 120. Therefore, the operator can help prevent the biological organs from being excessively tightened by the pulling unit 120.

In addition, the frame portion 110B can help prevent the frame portion 110B from performing the synechia with the biological organs other than the biological organs to be joined by the suppressing portion that suppresses the synechia with the biological organs.

Next, a modification example of the above-described embodiment will be described. In the description of the modification example, detailed description of the constituent members and the like already described in the above-described embodiment will be omitted. In addition, the contents not particularly described in the description of the modification example can be the same as those in the above-described embodiment.

Modification Example 1

Figure 4A:
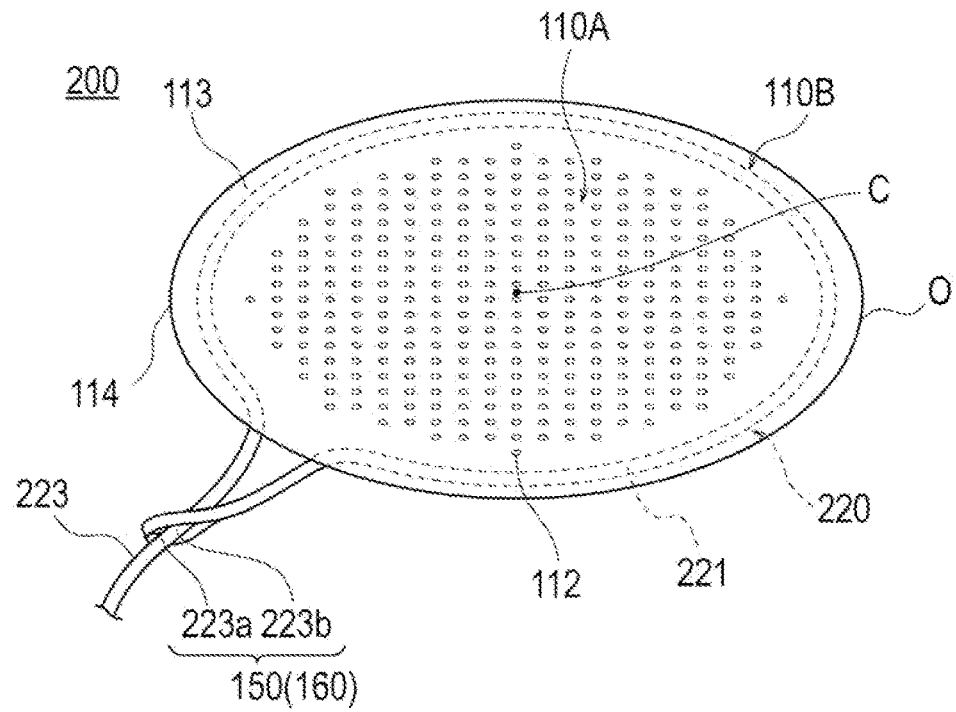
FIG. 4A is a perspective view illustrating Modification Example 1 of the medical device of the present disclosure.

FIG. 4A is a perspective view of a medical device 200 according to Modification Example 1, and FIGS. 4B-4G is a diagram for describing a shape example of the pulling unit 120 of the medical device 200 according to the modification example 1.

As illustrated in FIG. 4A, the pulling unit 220 included in the medical device 200 according to Modification Example 1 includes a strip-shaped member. The pulling unit 220 includes a connection section 221 connected to the frame portion 110B and a non-connection section 223 pulled out outside the adhesion promotion sheet 110. The non-connection section 223 is provided with the adjustment unit 150 configured to include an annular portion 223a and an insertion portion 223b inserted through the annular portion 223a.

Figure 4B:
FIGS. 4B-4G are plan views illustrating a shape example of a pulling unit including a strip-shaped member.
Figure 4C:
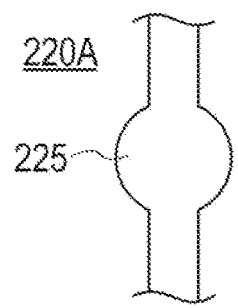
Figure 4D:
Figure 4E:
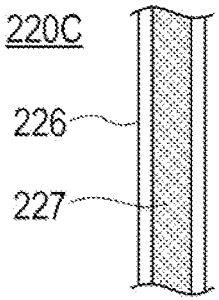
Figure 4F:
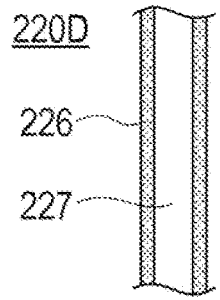
Figure 4G:
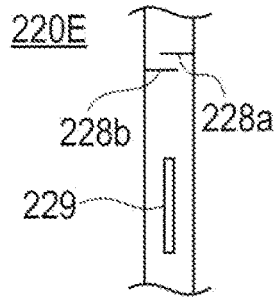

As illustrated in FIG. 4B, the pulling unit 220 can include a strip-shaped member extending linearly with a substantially constant width. In addition, as illustrated in FIG. 4C, the pulling unit 220A can include a strip-shaped member formed in a substantially central portion in the extending direction and having a projection portion 225 projecting in the width direction intersecting the extending direction. The pulling unit 220A can increase a holding force for holding the adhesion promotion sheet 110 on the biological organs as compared with the pulling unit 220. In addition, as illustrated in FIG. 4D, the pulling unit 220B can include a strip-shaped member formed in a shape in which the width gradually increases toward the substantially central portion in the extending direction. In a case where the pulling unit 220B is configured to be removable from the adhesion promotion sheet 110, the pulling unit 220B is likely to be released from the insertion (connection) with respect to the adhesion promotion sheet 110. In addition, as illustrated in FIGS. 4E and 4F, the rigidity may be configured to be different between the both end portions 226 and the central portion 227 in the width direction of each of the pulling units 220C and 220D. In accordance with an exemplary embodiment, the rigidity of a portion of each of the pulling units 220C and 220D can be made higher than that of the other portions, thus it is possible to help prevent each of the pulling units 220C and 220D from being damaged during the pulling operation. In addition, as illustrated in FIG. 4G, the pulling unit 220E may be provided with slits 228a and 228b extending in the width direction and a hole portion 229 formed in the central portion in the width direction and extending in the extending direction. The operator can regulate the pulling operation of the pulling unit 220E by passing the pulling unit 220E through the hole portion 229 and hooking the side surface portion of the pulling unit 220E into the slits 227a and 228b. Each pulling unit including the strip-shaped member may be formed in the same planar shape as the shape example of the string-shaped member illustrated in FIGS. 3A and 3B.

In the medical device 200, since the pulling unit 220 includes the strip-shaped member, the contact area between the pulling unit 220 and the pancreatic parenchyma B1 is larger than that in the case where the pulling unit 220 includes the string-shaped member. Therefore, the medical device 200 can increase the holding force of the adhesion promotion sheet 110 with respect to the pancreatic parenchyma B1.

Modification Example 2

Figure 5A:
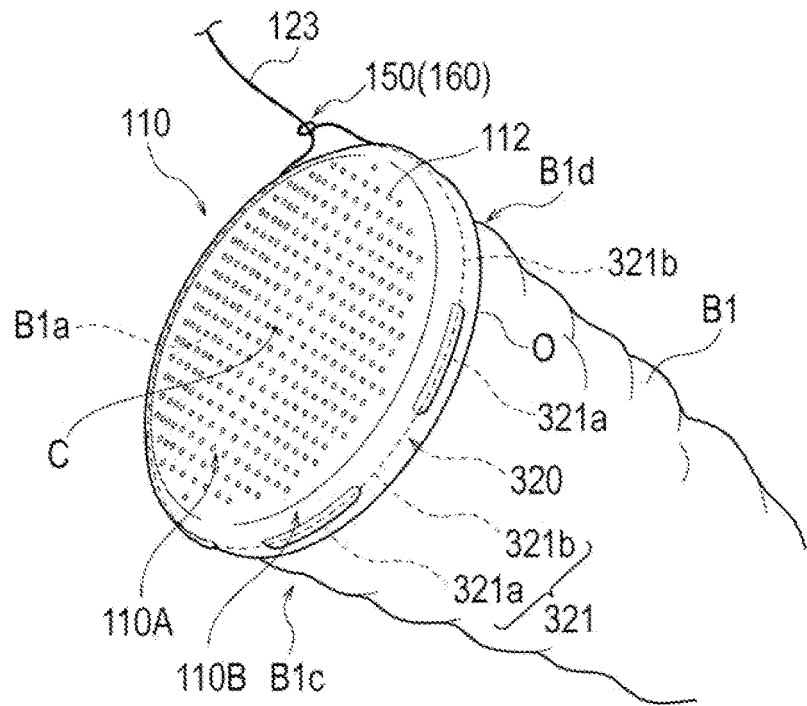
FIG. 5A is a perspective view illustrating a usage example of Modification Example 2 of the medical device of the present disclosure.

FIG. 5A is a perspective view for describing a usage example of a medical device according to Modification Example 2.

A connection section 321 of a pulling unit 320 can be configured to have a first site 321a having a rigidity higher than that of the non-connection section 123 and a second site 321b having a rigidity lower than that of the first site 321a. As illustrated in FIG. 5A, the first site 321a and the second site 321b can be alternately disposed along the circumferential direction of the adhesion promotion sheet 110. By including the first site 321a, the pulling unit 320 can increase the holding force for holding the adhesion promotion sheet 110 on the pancreatic parenchyma B1 on the posterior wall B1c (portion of the pancreatic parenchyma B1 on a dorsal side in the circumferential direction) side of the pancreatic parenchyma B1.

Modification Example 3

Figure 5B:
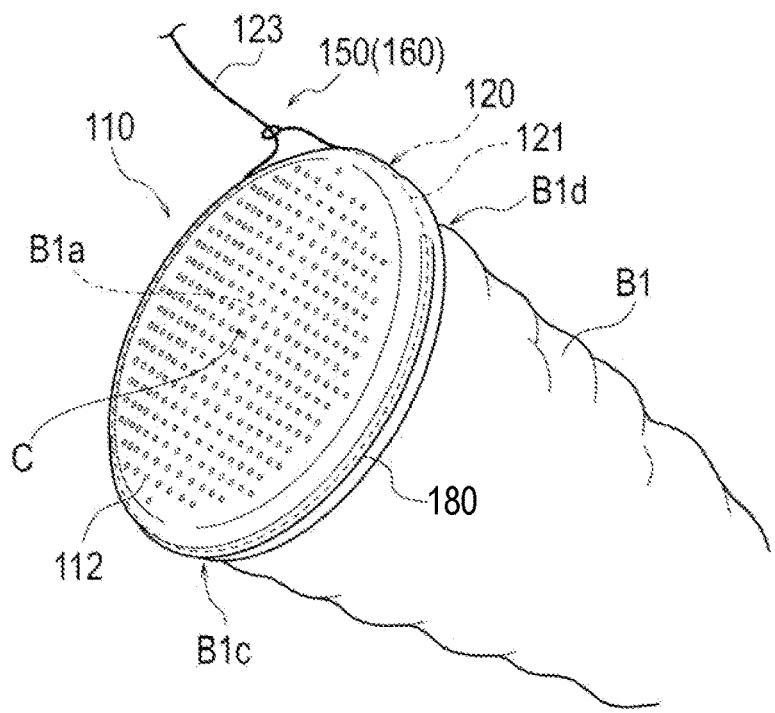
FIG. 5B is a perspective view illustrating a usage example of Modification Example 3 of the medical device of the present disclosure.

FIG. 5B is a perspective view for describing a usage example of a medical device according to Modification Example 3.

The medical device may include, for example, a holding member 180 that can be attached to the adhesion promotion sheet 110. The holding member 180 can include, for example, a member having a higher rigidity than that of the pulling unit 320. In addition, the holding member 180 can be configured to have a C-shaped outer shape that can be disposed along a portion of the outer peripheral surface on the posterior wall B1c (portion of the pancreatic parenchyma B1 on a dorsal side in the circumferential direction) side of the pancreatic parenchyma B1. The holding member 180 is disposed so as to be hooked on the pancreatic parenchyma B1, so that the operator can hold the adhesion promotion sheet 110 more stably on the pancreatic parenchyma B1.

Modification Example 4

Figure 6A:
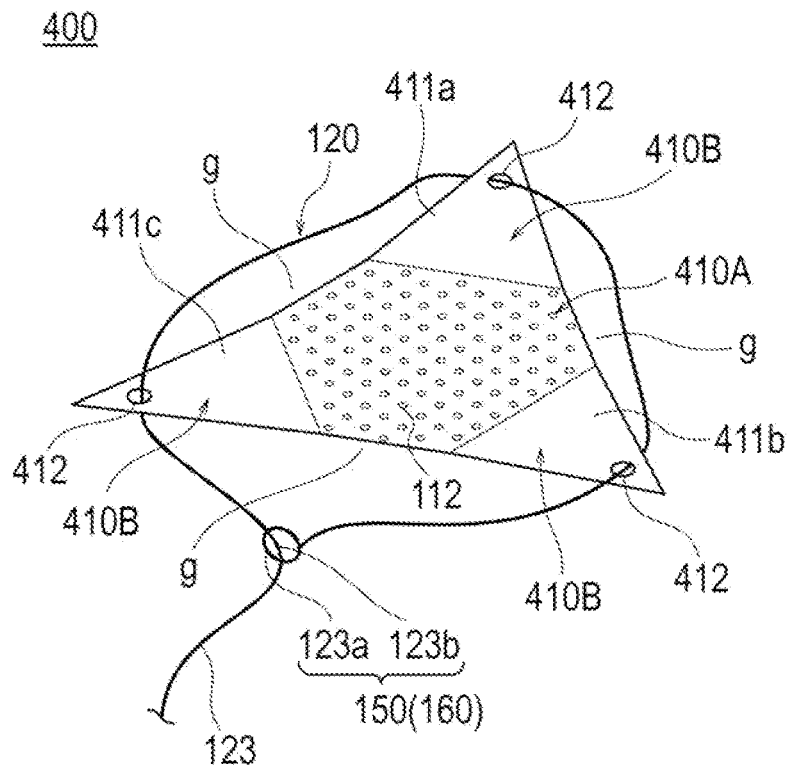
FIG. 6A is a perspective view illustrating Modification Example 4 of the medical device of the present disclosure.

FIG. 6A is a perspective view of a medical device 400 according to Modification Example 4.

A frame portion 410B of an adhesion promotion sheet 410 included in the medical device 400 according to Modification Example 4 includes a plurality of protruding portions 411a, 411b, and 411c disposed in the circumferential direction of the adhesion promotion sheet 410. Each of the protruding portions 411a, 411b, and 411c includes a hole portion 412 through which the pulling unit 120 can be inserted. A predetermined space (gap) g is formed between the protruding portions 411a, 411b, and 411c. In accordance with an exemplary embodiment, each of the protruding portions 411a, 411b and 411c has a substantially triangular planar shape.

The operator can deform each of the protruding portions 411a, 411b and 411c along the outer peripheral surface of the pancreatic parenchyma B1 by pulling the pulling unit 120. In addition, each of the protruding portions 411a, 411b and 411c is disposed so as to cover at least a portion of the outer peripheral surface of the pancreatic parenchyma B1. Each of the protruding portions 411a, 411b, and 411c may be rather easily deformed when the pulling operation is performed, as compared with the frame portion 110B (refer to FIG. 1A) described above. Therefore, each of the protruding portions 411a, 411b and 411c can be more reliably deformed along the outer peripheral surface of the pancreatic parenchyma B1.

Modification Example 5

Figure 6B:
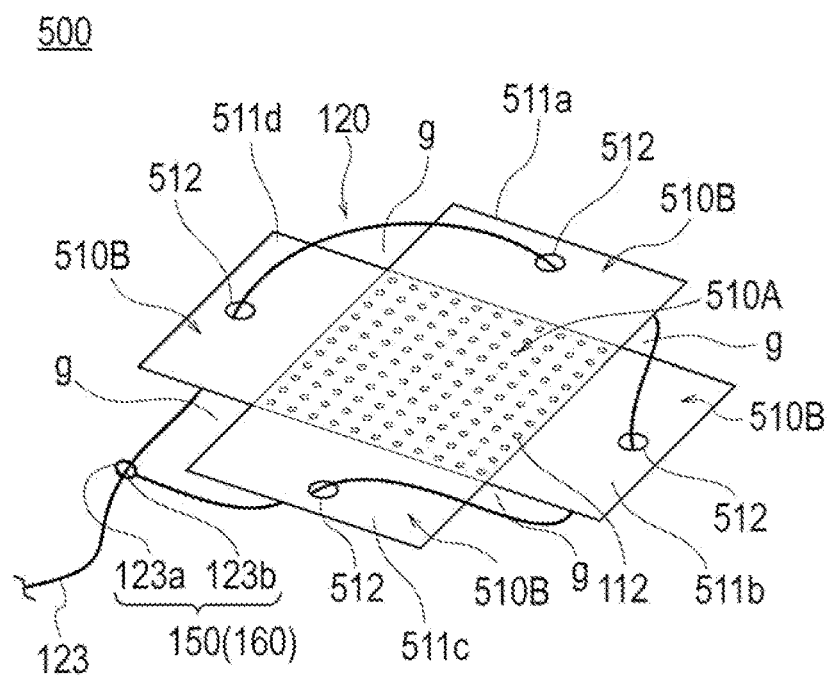
FIG. 6B is a perspective view illustrating Modification Example 5 of the medical device of the present disclosure.

FIG. 6B is a perspective view of a medical device 500 according to Modification Example 5.

A frame portion 510B of an adhesion promotion sheet 510 included in the medical device 500 according to Modification Example 5 includes four protruding portions 511a, 511b, 511c, and 511d. Each of the protruding portions 511a, 511b, 511c, and 511d includes a hole portion 512 through which the pulling unit 120 can be inserted. A predetermined space (gap) g is formed between the protruding portions 511a, 511b, 511c, and 511d. In accordance with an exemplary embodiment, each of the protruding portions 511a, 511b and 511c has a substantially rectangular planar shape. Similarly to the medical device 400 according to Modification Example 4, since each of the protruding portions 511a, 511b, 511c, and 511d is rather easily deformed when the pulling unit 120 is pulled, the medical device 500 according to Modification Example 5 can be reliably deformed along the outer peripheral surface of the pancreatic parenchyma B1. The shape, number, and the like of the protruding portions illustrated in Modification Examples 4 and 5 are not particularly limited.

Embodiment of Treatment Method (Biological Organs Anastomosis)

Next, a treatment method using the medical device will be described.

Figure 7:
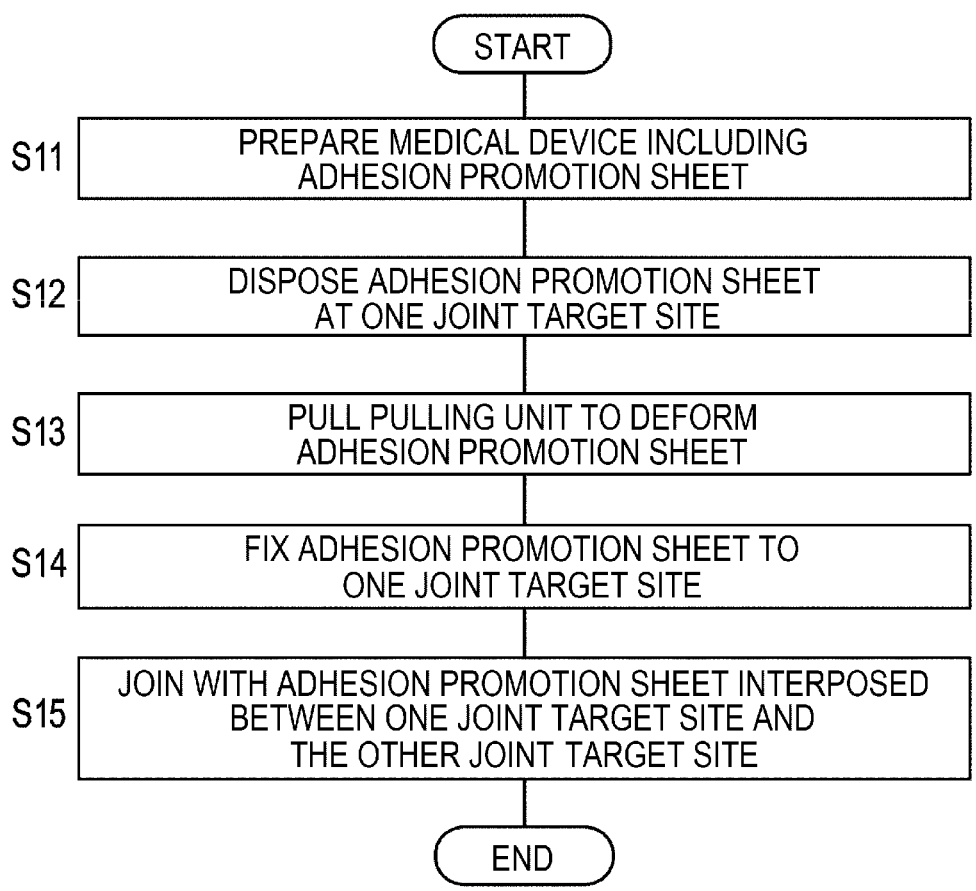
FIG. 7 is a flowchart illustrating each procedure of a treatment method using the medical device.

FIG. 7 is a flowchart illustrating each procedure of the treatment method using the medical device.

The treatment method includes preparing a medical device including an adhesion promotion sheet provided with a pulling unit (S11), disposing the adhesion promotion sheet at one joint target site (S12), pulling the pulling unit to deform the adhesion promotion sheet (S13), fixing the adhesion promotion sheet to the one joint target site (S14), and joining the one joint target site and the other joint target site in a state where at least a portion of the adhesion promotion sheet is disposed between the one joint target site and the other joint target site (S15).

The biological organs and the joint target site in the biological organs which are joined by using the treatment method are not particularly limited, and can be optionally selected. In the following description, pancreatic parenchyma-jejunum anastomosis will be described as an example. However, the above-described treatment method may be applied, for example, to large intestine anastomosis or gastric tube anastomosis. In addition, as the medical device used in each medical procedure described below, for example, it is possible to select any desired one from the medical devices described above. However, in the following description, as a representative example which can be used for each medical procedure, an example of using a specific medical device will be described. In addition, in each medical procedure described below, detailed description of known medical procedures, known medical devices, and medical instruments will be appropriately omitted.

Hereinafter, in the description herein, "disposing the adhesion promotion sheet between the biological organs" means at least any one of disposing the adhesion promotion sheet in a state of being in direct or indirect contact with the biological organs, disposing the adhesion promotion sheet in a state where a spatial gap is formed with the biological organs, and disposing the adhesion promotion sheet in both the states (for example, disposing the adhesion promotion sheet in a state where the adhesion promotion sheet is in contact with one biological organ and the adhesion promotion sheet is not in contact with the other biological organ). In addition, in the description herein, a "periphery" does not define a strict range (region), and means a predetermined range (region) as long as a treatment purpose (joining the biological organs to each other) can be achieved. In addition, as long as the treatment purpose can be achieved, in the medical procedure described in the respective treatment methods, orders can be appropriately switched among the order of the respective treatment methods.

Embodiment of Treatment Method (Pancreatic Parenchyma-Jejunum Anastomosis)

Figure 8:
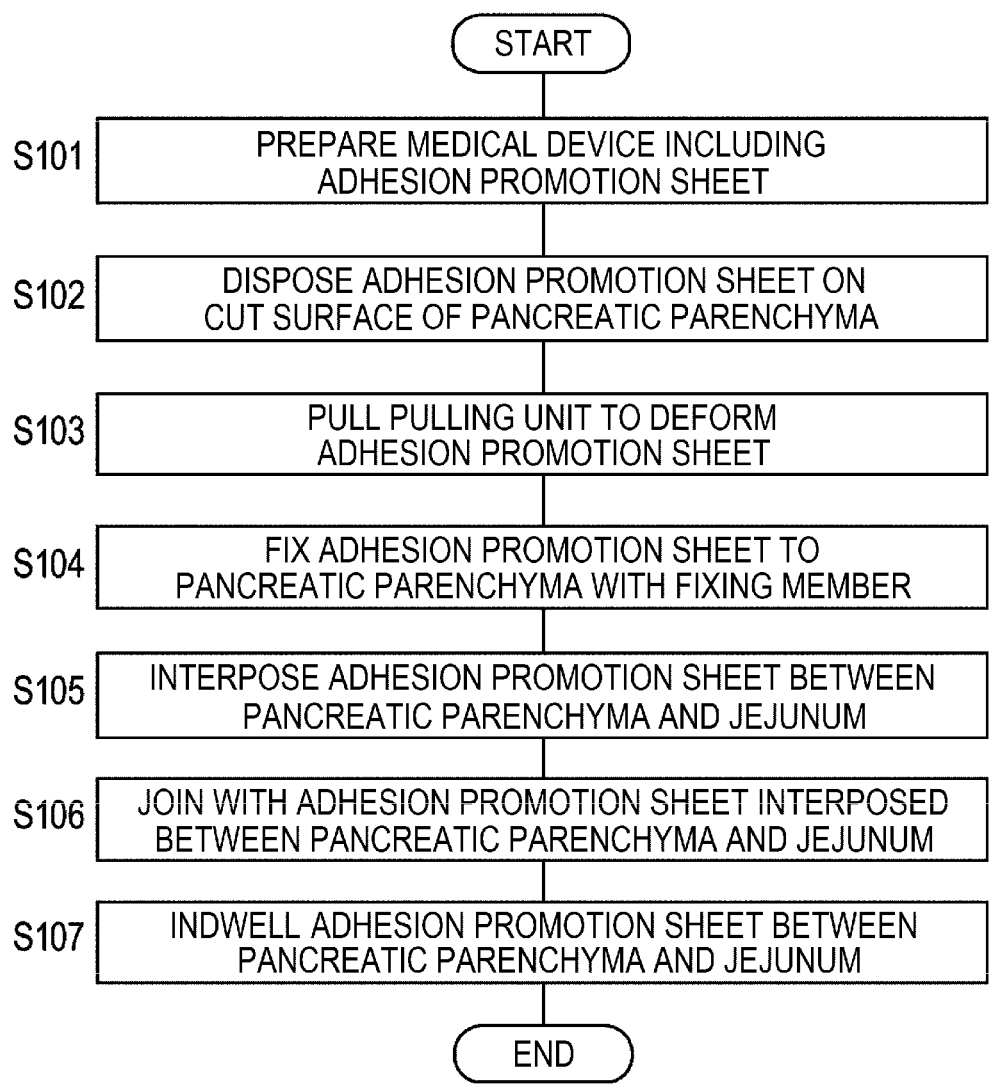
FIG. 8 is a flowchart illustrating a procedure of an embodiment of the treatment method (pancreatic parenchyma-jejunum anastomosis).

FIG. 8 is a flowchart illustrating a procedure of an embodiment of the treatment method (pancreatic parenchyma-jejunum anastomosis), and FIGS. 9 to 16 are diagrams used for describing the pancreatic parenchyma-jejunum anastomosis.

In the treatment method according to the present embodiment, the biological organs to be joined are the pancreatic parenchyma B1 after pancreaticoduodenectomy and the jejunum B2. In the following description, a procedure of joining the periphery of the cut surface B1a of the cut pancreatic parenchyma B1 (one joint target site) and a predetermined site of an intestinal wall of the jejunum B2 (the other joint target site) will be described. In addition, in the present embodiment, the usage example of the medical device 100 illustrated in FIG. 1A will be described.

As illustrated in FIG. 8, the treatment method according to the present embodiment includes preparing the medical device 100 including the adhesion promotion sheet 110 provided with the pulling unit 120 (S101), disposing the adhesion promotion sheet 110 on the cut surface B1a of the pancreatic parenchyma B1 (S102), pulling the pulling unit 120 to deform the adhesion promotion sheet 110 (S103), fixing the adhesion promotion sheet with a fixing member (S104), interposing the adhesion promotion sheet 110 between the pancreatic parenchyma B1 and the jejunum B2 (S105), joining with the adhesion promotion sheet 110 interposed between the pancreatic parenchyma B1 and the jejunum B2 (S106), and indwelling the adhesion promotion sheet 110 between the pancreatic parenchyma B1 and the jejunum B2 (S107).

Next, an example of the treatment method according to the present embodiment will be specifically described with reference to FIGS. 9 to 16. In FIG. 14, a plurality of both end needles 920a to 920e described later are omitted.

Figure 9:
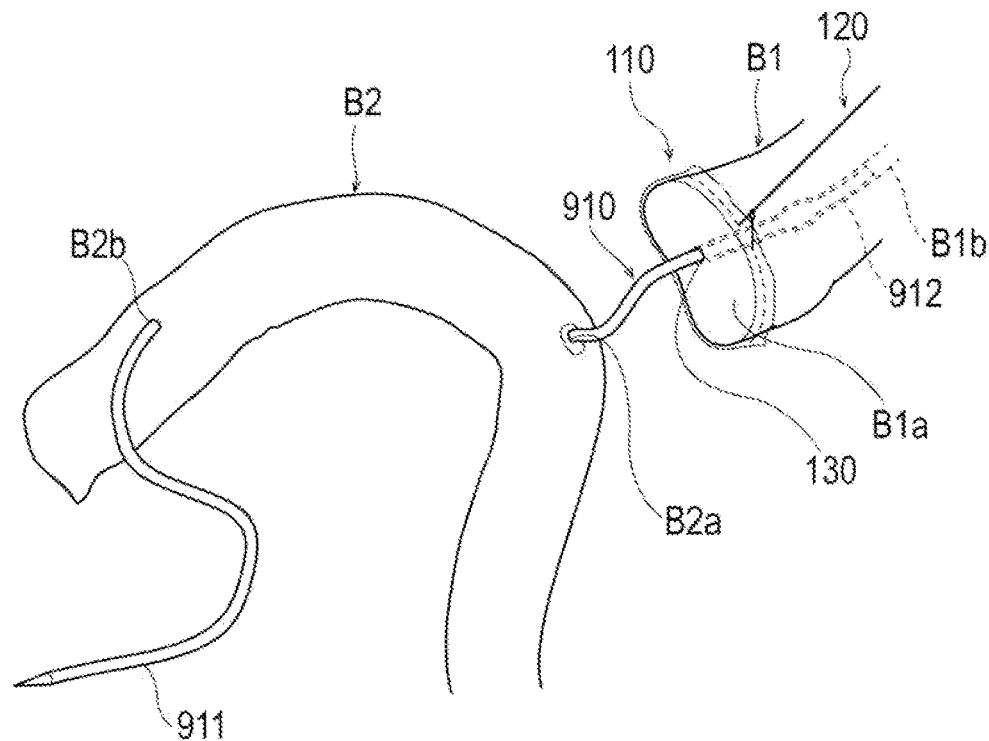
FIG. 9 is a schematic perspective view for describing the pancreatic parenchyma-jejunum anastomosis.

As illustrated in FIG. 9, the operator causes the rear surface 114 (or front surface 113) of the adhesion promotion sheet 110 face the cut surface B1a of the pancreatic parenchyma B1. The operator disposes the non-connection section 123 so as to not to cover the cut surface B1a of the pancreatic parenchyma B1 in the plane direction. The operator can deform the adhesion promotion sheet 110 so that the frame portion 110B covers a portion of the outer peripheral surface of the pancreatic parenchyma B1 by pulling the pulling unit 120. The operator can hold the adhesion promotion portion 110A in close contact with the cut surface B1a of the pancreatic parenchyma B1 (refer to FIG. 1B) by performing such an operation.

When disposing the adhesion promotion sheet 110 on the cut surface B1a of the pancreatic parenchyma B1, the operator can adopt the following work procedure. First, the operator forms a hole portion 130 in the adhesion promotion sheet 110 by pressing an end portion 911 (or end portion 912) of a pancreatic duct tube 910 against the adhesion promotion sheet 110. In addition, the operator inserts the pancreatic duct tube 910 into the jejunum B2 so that the end portion 911 of the pancreatic duct tube 910 passes through the inside of the jejunum B2 from the through-hole B2a at the planned anastomosis site of jejunum B2 and exits the outside of the jejunum B2 from the through-hole B2b of the jejunum B2.

Next, the operator temporarily inserts the end portion 912 of the pancreatic duct tube 910 into the pancreatic duct B1b of the pancreatic parenchyma B1 in a state where the pancreatic duct tube 910 inserts the hole portion 130 of the adhesion promotion sheet 110 and holds the adhesion promotion sheet 110.

As the pancreatic duct tube 910, for example, a resin tube in which a bump (projection portion) for preventing falling off is formed at the end portion 912 can be used. The pancreatic duct tube 910 temporarily inserted into the pancreatic duct B1b suppresses the leakage of body fluid such as pancreatic juice from the pancreatic duct B1b during the medical procedure. According to such a procedure, the operator can dispose the adhesion promotion sheet 110 and temporarily insert the pancreatic duct tube 910 at the same time.

In addition, the operator may use a device other than the pancreatic duct tube 910 when forming the hole portion 130 for inserting the pancreatic duct tube 910. In addition, the hole portion 130 through which the pancreatic duct tube 910 is inserted may be formed in the adhesion promotion sheet 110 in advance in a state before use. In addition, the operator may temporarily insert the pancreatic duct tube 910 into the pancreatic duct B1b after disposing the adhesion promotion sheet 110 on the cut surface B1a of the pancreatic parenchyma B1.

Next, the operator fixes the adhesion promotion sheet 110 to the pancreatic parenchyma B1 with the fixing member. In the following description, an example of a procedure of fixing the adhesion promotion sheet 110 to the pancreatic parenchyma B1 by using the plurality of the both end needles 920a to 920e with sutures as fixing members will be described. As the both end needles 920a to 920e, needles having a bioabsorbable absorbent thread (suture) and a biocompatible needle portion attached to both ends of the absorbent thread can be used. Both end needles 930 and 940a to 940e described later are also configured to include absorbent threads and needle portions.

Figure 10:
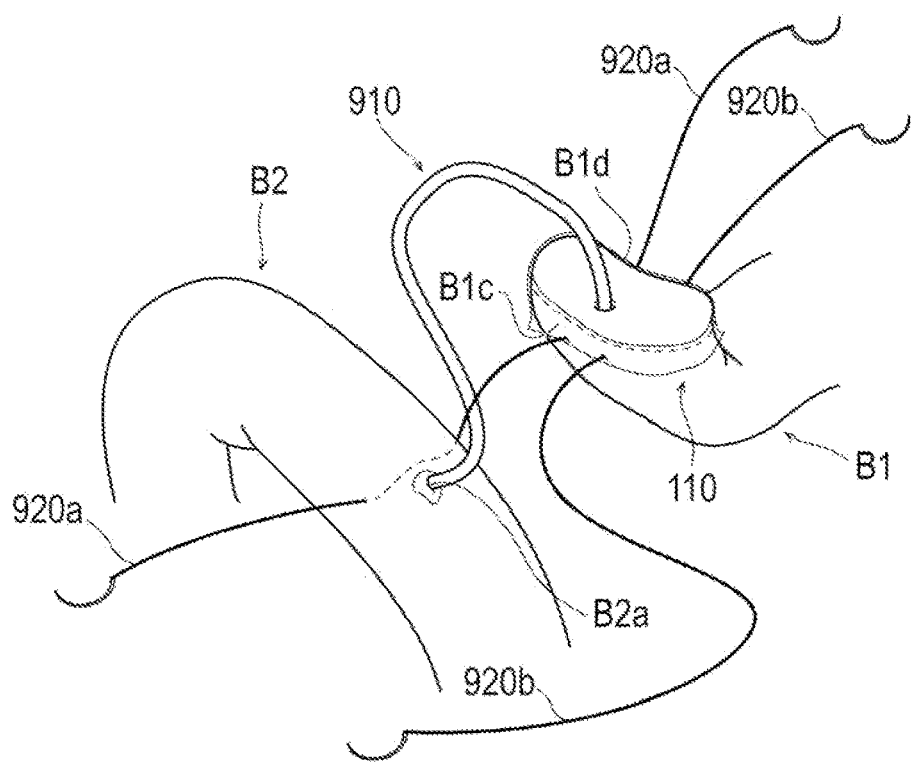
FIG. 10 is a schematic perspective view for describing the pancreatic parenchyma-jejunum anastomosis.
Figure 11:
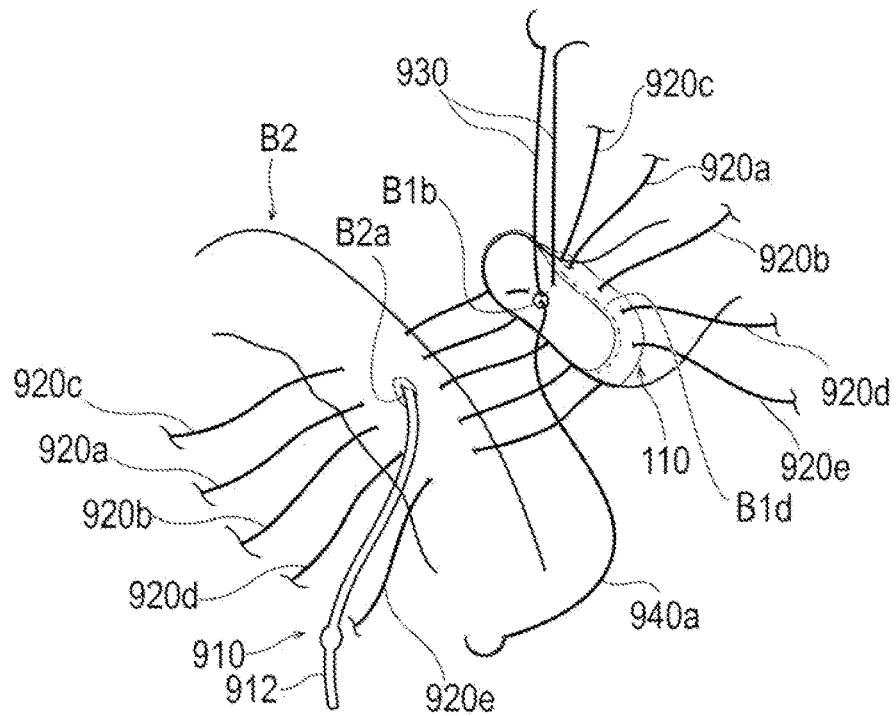
FIG. 11 is a schematic perspective view for describing the pancreatic parenchyma-jejunum anastomosis.

First, as illustrated in FIG. 10, the operator moves the both end needle 920a from the posterior wall B1c of the pancreatic parenchyma B1 (portion of the pancreatic parenchyma B1 on a dorsal side in the circumferential direction) and the portion disposed on the posterior wall B1c in the adhesion promotion sheet 110 toward the anterior wall B1d of the pancreatic parenchyma B1 and the portion disposed on the anterior wall B1d in the adhesion promotion sheet 110 in a state where the adhesion promotion sheet 110 is held on the pancreatic parenchyma B1. Next, the operator moves the both end needle 920a so as to insert a jejunal serosal muscular layer at the planned anastomosis site of the jejunum B2 (periphery of the through-hole B2a). The operator repeats such an operation, and as illustrated in FIG. 11, inserts the plurality of the both end needles 920a to 920e into the plurality of the both end needles 920a to 920e on the adhesion promotion sheet 110, the pancreatic parenchyma B1, and the jejunal serosal muscular layer of the jejunum B2. In this manner, the operator can fix the adhesion promotion sheet 110 to the pancreatic parenchyma B1 by using the plurality of the both end needles 920a to 920e that suture the pancreatic parenchyma B1 and the jejunum B2.

The operator may appropriately separate the pulling unit 120 from the adhesion promotion sheet 110 after fixing the adhesion promotion sheet 110 to the cut surface B1a of the pancreatic parenchyma B1. The operator pulls the pulling unit 120 until the adhesion promotion sheet 110 is fixed to the cut surface B1a of the pancreatic parenchyma B1 and maintains a state where the frame portion 110B of the adhesion promotion sheet 110 is in close contact with the outer peripheral surface of the pancreatic parenchyma B1. Accordingly, it is possible to help prevent the adhesion promotion sheet 110 from misaligning or falling off from the pancreatic parenchyma B1.

The number of both end needles to be inserted into the pancreatic parenchyma B1 and the jejunal serosal muscular layer of the jejunum B2 and the positions through which the both end needles are inserted are not particularly limited. In addition, the operator may fix the adhesion promotion sheet 110 to the pancreatic parenchyma B1 by using a biodegradable stapler or the like as a fixing member instead of the plurality of the both end needles 920a to 920e.

Next, as illustrated in FIG. 11, the operator removes the end portion 912 of the pancreatic duct tube 910 from the pancreatic duct B1b.

Next, as illustrated in FIG. 11, the operator passes the both end needle 930 from a luminal side of the pancreatic duct B1b toward the anterior wall B1d side of the cut surface B1a of the pancreatic parenchyma B1. The both end needle 930 is held by a gripping instrument such as tweezers so as not to interfere with the medical procedure in a state where the jejunum B2 is not inserted.

Figure 12:
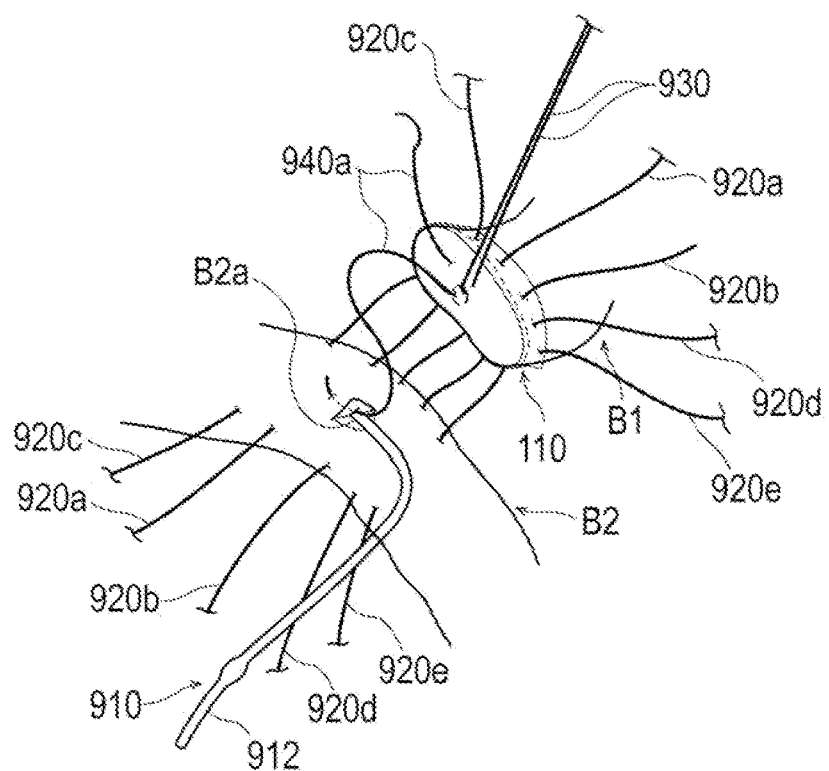
FIG. 12 is a schematic perspective view for describing the pancreatic parenchyma-jejunum anastomosis.
Figure 13:
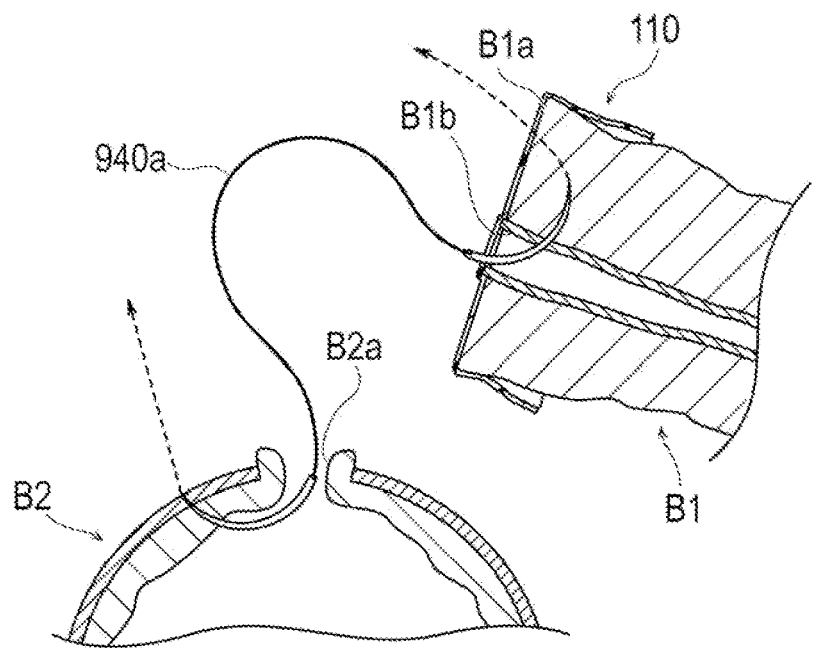
FIG. 13 is a schematic cross-sectional view for describing the pancreatic parenchyma-jejunum anastomosis.
Figure 14:
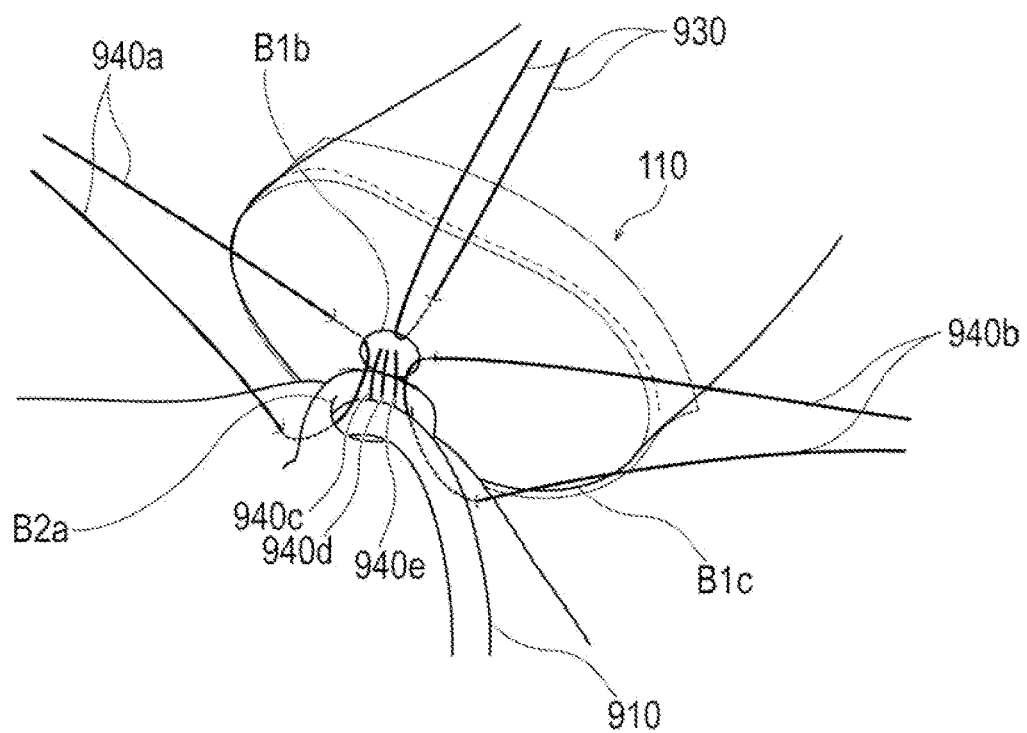
FIG. 14 is a schematic perspective view for describing the pancreatic parenchyma-jejunum anastomosis.

Next, as illustrated in FIGS. 11 and 13, the operator moves one end of the both end needle 940a from the luminal side of the pancreatic duct B1b toward the cut surface B1a of the pancreatic parenchyma B1. Next, as illustrated in FIGS. 12 and 13, the operator inserts the other end of the both end needle 940a into the through-hole B2a of the jejunum B2, and moves the other end of the both end needle 940a from the inside of the jejunum B2 toward the outside of the jejunum B2. As illustrated in FIG. 14, the operator inserts the plurality of both end needles 940a to 940e into different sites of the pancreatic duct B1b in the circumferential direction and the jejunum B2. FIG. 13 is a cross-sectional view schematically illustrating a portion of the pancreatic parenchyma B1 and the jejunum B2 before being anastomosed.

Next, as illustrated in FIG. 14, the operator brings the posterior wall B1c of the pancreatic parenchyma B1 and the pancreatic duct B1b into close contact with the planned anastomosis site of the jejunum B2. Of the plurality of the both end needles 940a to 940e, the both end needles 940c to 940e that insert the dorsal side (posterior wall B1c side) of the pancreatic duct B1b in the circumferential direction are ligated.

Figure 15:
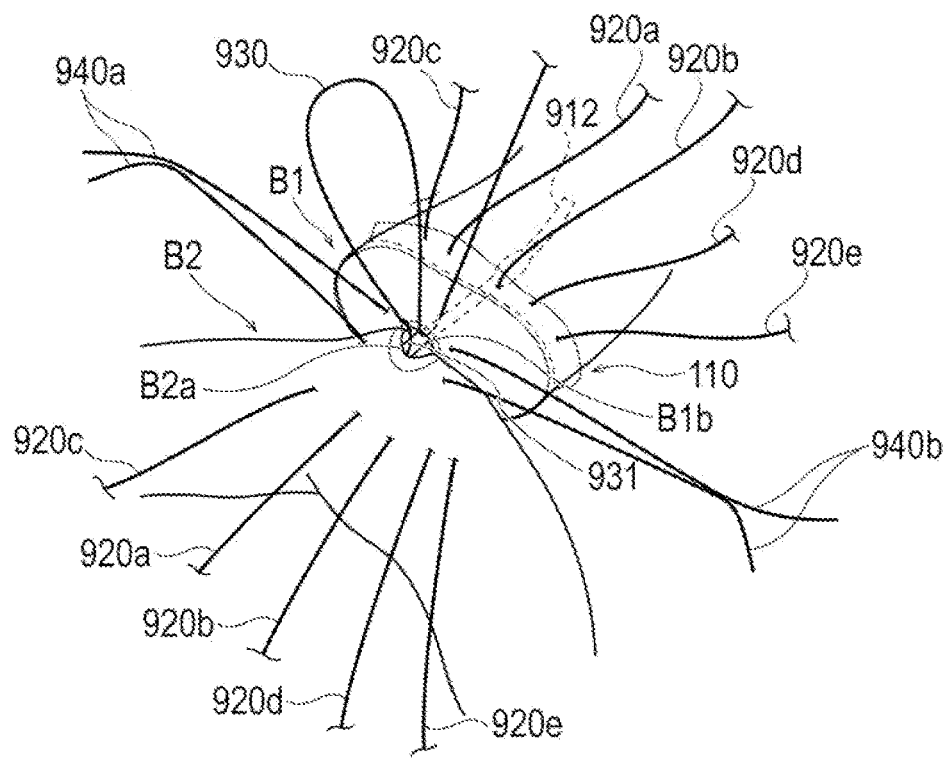
FIG. 15 is a schematic perspective view for describing the pancreatic parenchyma-jejunum anastomosis.

Next, as illustrated in FIG. 15, the operator reinserts the end portion 912 of the pancreatic duct tube 910 into the pancreatic duct B1b. Next, the operator inserts a needle portion 931 extending from the inside of the pancreatic duct B1b in the both end needle 930 into the through-hole B2b formed in the jejunum B2, and moves the needle portion 931 from the inside of the jejunum B2 toward the outside of the jejunum B2.

Next, the operator ligates the both end needles 930, 940a, and 940b (not illustrated). The number of both end needles to be inserted into the pancreatic duct B1b and the jejunum B2 and the positions through which the both end needles are inserted are not particularly limited.

Figure 16:
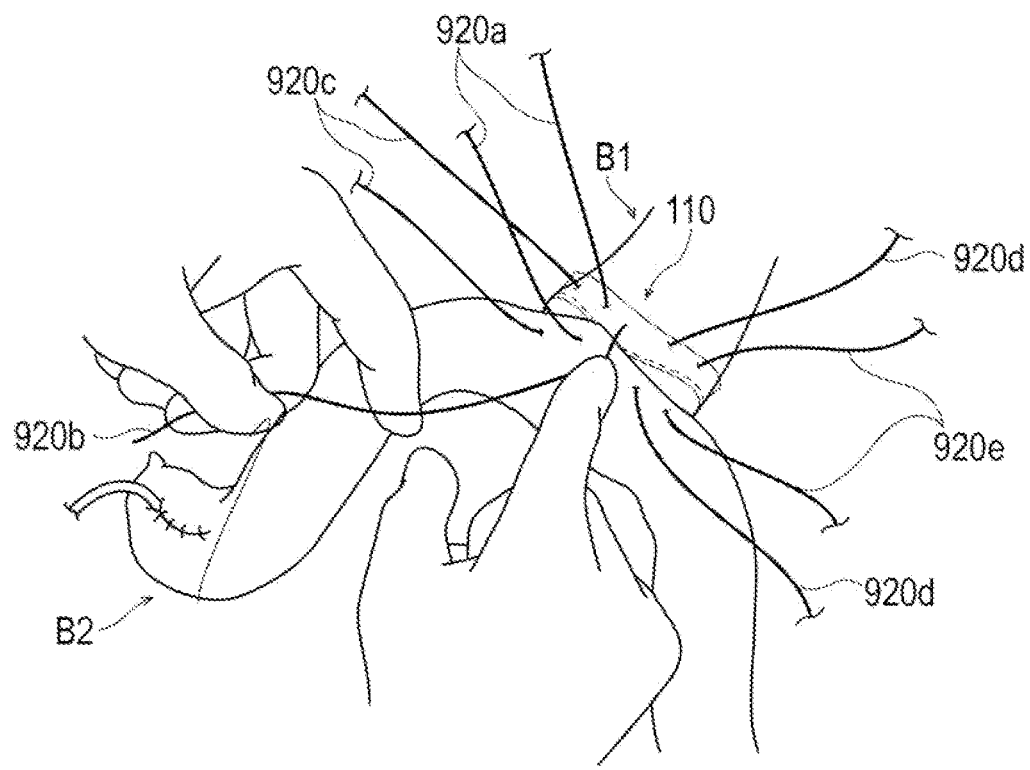
FIG. 16 is a schematic perspective view for describing the pancreatic parenchyma-jejunum anastomosis.

Next, as illustrated in FIG. 16, the operator ligates the both end needles 920a to 920e while pressing the jejunum B2 against the pancreatic parenchyma B1 with the operator's finger. As a result, the pancreatic parenchyma B1 and the jejunum B2 are sutured in a state where the adhesion promotion sheet 110 is interposed between the pancreatic parenchyma B1 and the jejunum B2. The jejunum B2 is deformed by the tension generated at the time of suturing so as to enclose the cut surface B1a of the pancreatic parenchyma B1 and the adhesion promotion portion 110A of the adhesion promotion sheet 110.

The operator indwells the adhesion promotion sheet 110 in a state where the adhesion promotion portion 110A of the adhesion promotion sheet 110 is interposed between the cut surface B1a of the pancreatic parenchyma B1 and the intestinal wall of the jejunum B2. The adhesion promotion portion 110A of the adhesion promotion sheet 110 is indwelled between the cut surface B1a of the pancreatic parenchyma B1 and the intestinal wall of the jejunum B2 while being in contact with the cut surface B1a of the pancreatic parenchyma B1 and the intestinal wall of the jejunum B2. Accordingly, the adhesion of the biological tissue of the pancreatic parenchyma B1 and the biological tissue of the intestinal wall of the jejunum B2 is promoted.

As described above, the treatment method according to the present embodiment is applied to the medical procedure of joining the pancreatic parenchyma B1 and the jejunum B2. In addition, in the above treatment method, the periphery of the cut surface B1a of the cut pancreatic parenchyma B1 and the intestinal wall (jejunal serosal muscular layer) of the jejunum B2 are joined to each other. According to the treatment method, the adhesion promotion portion 110A of the adhesion promotion sheet 110 interposed between the cut surface B1a of the pancreatic parenchyma B1 and the intestinal wall of the jejunum B2 can promote the adhesion of the biological tissue of the pancreatic parenchyma B1 and the biological tissue of the intestinal wall of the jejunum B2, and can reduce the risk of anastomotic leakage after the pancreatic parenchyma-jejunum anastomosis.

In addition, the operator can help prevent the adhesion promotion sheet 110 from being distorted or misaligned by deforming the frame portion 110B of the adhesion promotion sheet 110 so as to cover at least a portion of the outer peripheral surface of the pancreatic parenchyma B1 by the pulling unit 120.

Another Modification Example

Next, a pulling unit 620 according to another modification example will be described with reference to FIGS. 17 to 22.

In the description of the present modification example, the description of the content that overlaps with the content already described in the above-described embodiment will be omitted. In addition, the contents not particularly described in the description of the modification example can be the same as those in the above-described embodiment.

Figure 17:
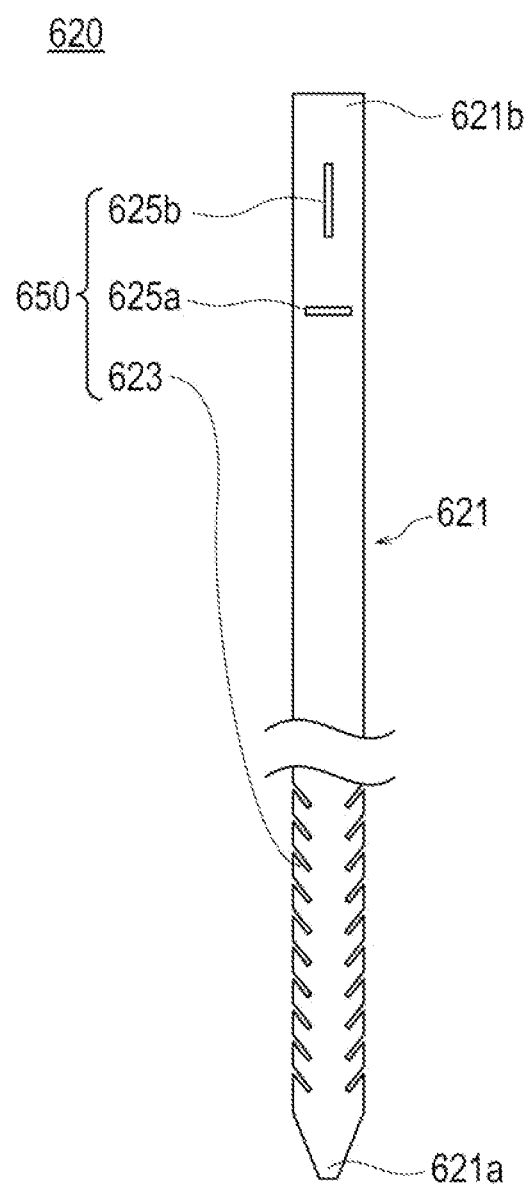
FIG. 17 is a plan view illustrating a pulling unit according to another modification example.

FIG. 17 illustrates a plan view of a pulling unit 620 in a state before being connected to the adhesion promotion sheet 110. FIGS. 18 to 22 illustrate a procedure example of the medical procedure using the medical device 100 provided with the pulling unit 620.

As illustrated in FIG. 17, the pulling unit 620 includes a strip-shaped main body portion 621 having a predetermined width and length, a plurality of slit portions 623 formed on one end portion 621a in the longitudinal direction of the main body portion 621, and a first hole portion 625a and a second hole portion 625b formed on the other end portion 621b in the longitudinal direction of the main body portion 621.

The one end portion 621a of the main body portion 621 can be formed, for example, into a tapered shape that tapers toward the tip end side of the one end portion 621a. By providing such a shape, the work of passing the one end portion 621a of the main body portion 621 through each of the hole portions 625a and 625b can be rather easily performed (refer to FIGS. 19 and 20).

The first hole portion 625a is disposed closer to the one end portion 621a of the main body portion 621 than the second hole portion 625b. The first hole portion 625a and the second hole portion 625b extend in directions orthogonal to each other. The first hole portion 625a extends substantially parallel to the width direction (horizontal direction in FIG. 17) of the main body portion 621. The second hole portion 625b extends substantially parallel to the longitudinal direction (vertical direction in FIG. 17) of the main body portion 621.

The first hole portion 625a can be formed, for example, in a substantially rectangular shape in which long sides are disposed along the width direction of the main body portion 621 in the plan view illustrated in FIG. 17. The second hole portion 625b can be formed, for example, in a substantially rectangular shape in which long sides are disposed along the longitudinal direction of the main body portion 621 in the plan view illustrated in FIG. 17. The shape, position, and size of each of the hole portions 625a and 625b are not particularly limited.

The slit portion 623 is inclined and extends in a direction parallel to the longitudinal direction of the main body portion 621. Specifically, the slit portion 623 is inclined from the center side of the main body portion 621 toward the outside. The number and shape of the slit portions 623, the specific position provided in the main body portion 621, and the like are not particularly limited.

Figure 18:
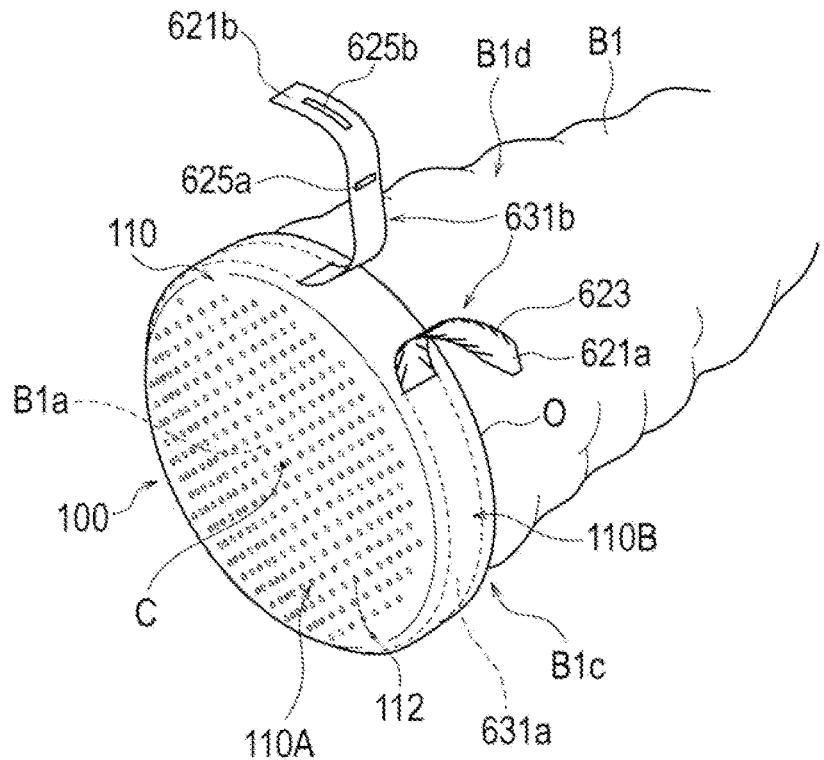
FIG. 18 is a diagram schematically illustrating a usage example of a medical device provided with the pulling unit according to another modification example.

As illustrated in FIG. 18, a portion of the main body portion 621 constitutes a connection section 631a connected to the frame portion (second region) 110B of the adhesion promotion sheet 110. The connection section 631a can be slidably connected to, for example, the frame portion 110B, similarly to the connection section 121 (refer to FIG. 1B) described in the above-described embodiment. In addition, as illustrated in FIG. 18, a portion of the main body portion 621 constitutes a non-connection section 631b that is not connected to the frame portion 110B of the adhesion promotion sheet 110.

Figure 22:
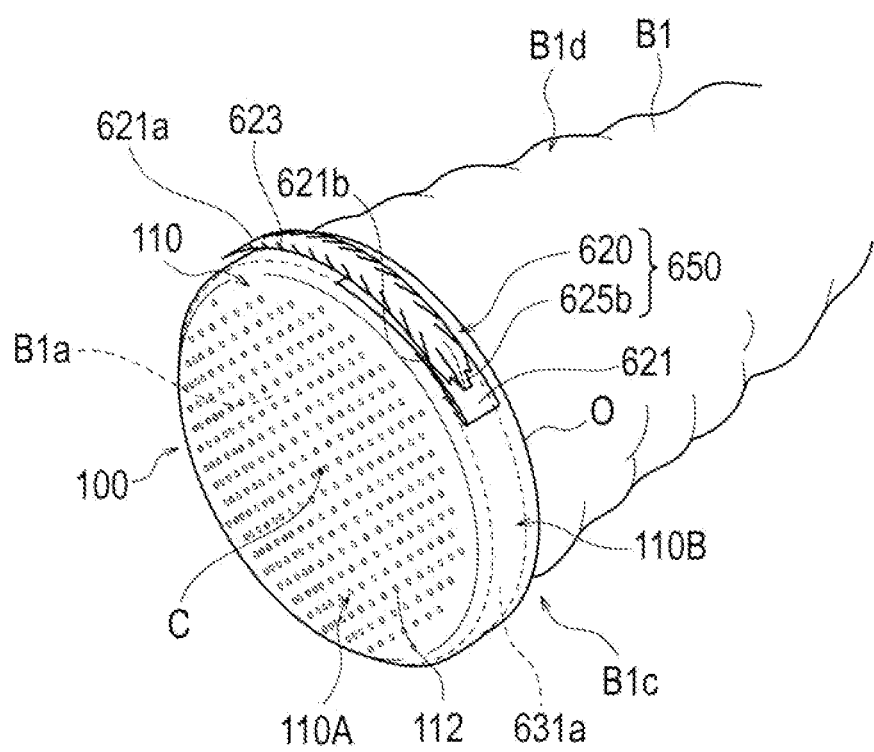
FIG. 22 is a diagram schematically illustrating a usage example of the medical device provided with the pulling unit according to another modification example.

As illustrated in FIG. 22, the slit portion 623 and each of the hole portions 625a and 625b disposed in the non-connection section 631b have a function as an adjustment unit 650 that can adjust the amount of deformation of the frame portion 110B of the adhesion promotion sheet 110.

Next, with reference to FIGS. 18 to 22, an example of the procedure of the medical procedure using the medical device 100 provided with the pulling unit 620 will be described. The procedure and the like already described in the above-described embodiment will be omitted as appropriate.

As illustrated in FIG. 18, the operator disposes the adhesion promotion portion 110A of the adhesion promotion sheet 110 on the cut surface B1a of the pancreatic parenchyma B1. The operator deforms the adhesion promotion sheet 110 by pulling both end portions 621b and 621b located at the non-connection section 631b of the pulling unit 620, and covers a portion of the outer peripheral surface of the pancreatic parenchyma B1 with the frame portion 110B of the adhesion promotion sheet 110.

Figure 19:
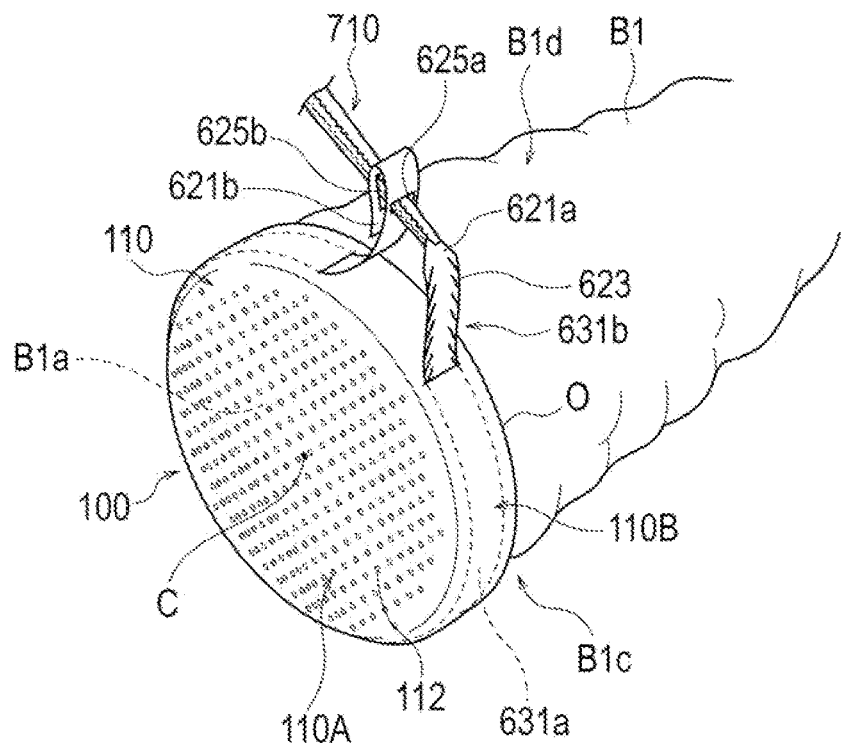
FIG. 19 is a diagram schematically illustrating a usage example of the medical device provided with the pulling unit according to another modification example.
Figure 20:
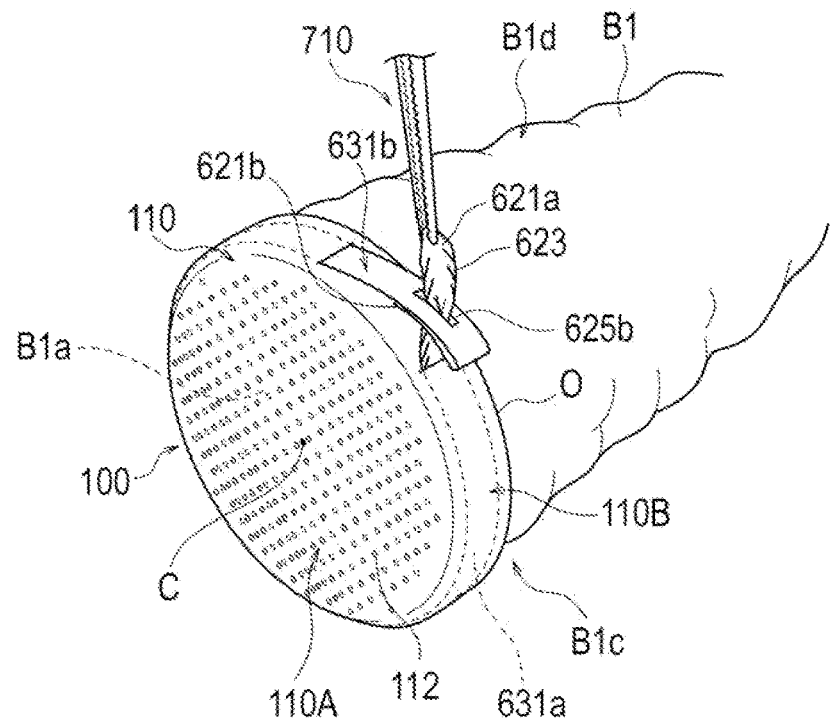
FIG. 20 is a diagram schematically illustrating a usage example of the medical device provided with the pulling unit according to another modification example.

As illustrated in FIGS. 19 and 20, the operator inserts a portion of the main body portion 621 on the one end portion 621a side into each of the hole portions 625a and 625b. When inserting a portion of the main body portion 621 on the one end portion 621a side into each of the hole portions 625a and 625b, the operator deforms a portion of the main body portion 621 on the other end portion 621b side so as to be folded back. The operator can use, for example, a medical instrument 710 such as forceps when performing such an operation. Specifically, as illustrated in FIG. 20, the operator operates to lift the medical instrument 710 while grasping a portion of the main body portion 621 on the one end portion 621a side with the medical instrument 710 passed through each of the hole portions 625a and 625b, as illustrated in FIG. 19. By performing such an operation, the operator can rather easily pass a portion of the main body portion 621 on the one end portion 621a side together with the medical instrument 710 through each of the hole portions 625a and 625b.

Figure 21:
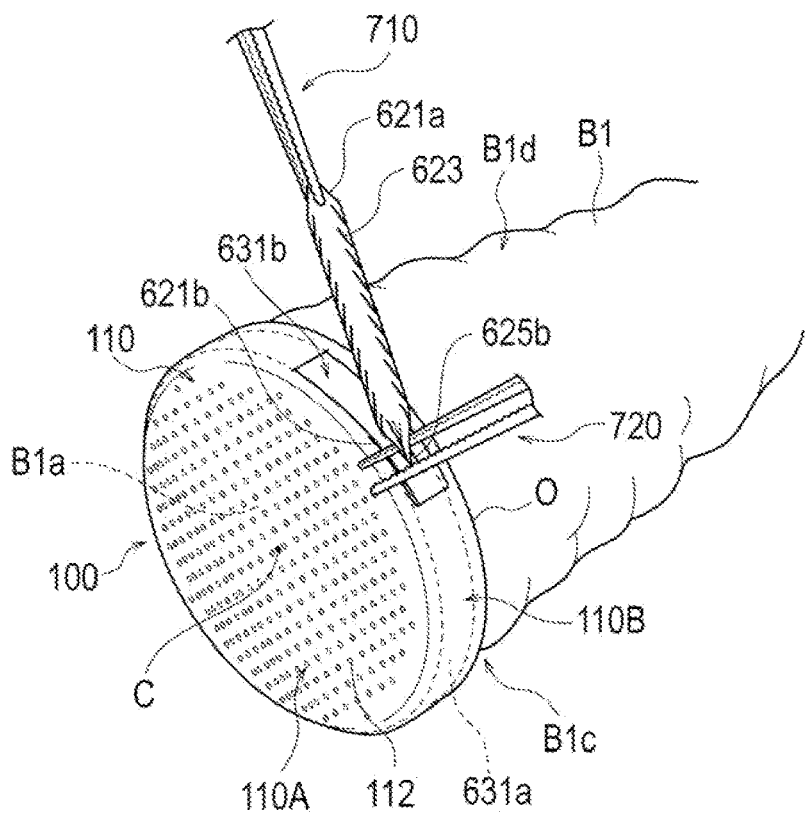
FIG. 21 is a diagram schematically illustrating a usage example of the medical device provided with the pulling unit according to another modification example.

As illustrated in FIG. 21, the operator pulls the portion inserted through each of the hole portions 625a and 625b in the main body portion 621, while pressing a portion where each of the hole portions 625a and 625b is disposed in the main body portion 621 and the peripheral portions thereof, by using a medical instrument 720 such as forceps. Accordingly, the adhesion promotion sheet 110 can be held on the pancreatic parenchyma B1.

Even when the operator releases the pulling of the pulling unit 620, the slit portion 623 is maintained in a state of being hooked by the first hole portion 625a and the second hole portion 625b. Therefore, the holding force for holding the adhesion promotion sheet 110 on the pancreatic parenchyma B1 can be maintained.

In the present modification example, the first hole portion 625a disposed at a position closer to the pancreatic parenchyma B1 than the second hole portion 625b (position closer to the outer peripheral surface of the pancreatic parenchyma B1) extends along the width direction of the pulling unit 620 (refer to FIG. 17). In addition, as illustrated in FIGS. 19 and 22, the first hole portion 625a is disposed along the extending direction of the pancreatic parenchyma Ba. Therefore, the operator can help prevent the main body portion 621 of the pulling unit 620 from being deformed so that the width of the portion inserted through the first hole portion 625a can be excessively reduced. Therefore, in the main body portion 621 of the pulling unit 620, the load applied to the pancreatic parenchyma Ba by the portion inserted through the first hole portion 625a can be suppressed to reduce the applied load. On the other hand, the second hole portion 625b disposed at a position further separated from the pancreatic parenchyma B1 than the first hole portion 625a (position separated from the outer peripheral surface of the pancreatic parenchyma B1) extends in a direction intersecting the width direction of the pulling unit 620 (refer to FIG. 17). Therefore, the portion inserted through the second hole portion 625*b* in the main body portion 621 of the pulling unit 620 is deformed so that the width is reduced along the shape of the second hole portion 625*b* having a smaller width. The main body portion 621 having a width larger than that of the second hole portion 625*b* is inserted into the second hole portion 625*b* having a smaller width. Accordingly, the hooking between the inner peripheral portion of the second hole portion 625*b* and the main body portion 621 is increased. Therefore, the holding force of the adhesion promotion sheet 110 with respect to the pancreatic parenchyma B1 can be effectively increased.

As illustrated in FIG. 22, the operator can wrap the one end portion 621*a* side inserted through the first hole portion 625*a* and the second hole portion 625*b* in the main body portion 625 around the pancreatic parenchyma Ba. The above portion of the main body portion 625 may be excised.

As described above, according to the medical device 100 provided with the pulling unit 620 according to the present modification example, the holding force of the adhesion promotion sheet 110 on the pancreatic parenchyma Ba can be effectively increased while reducing the load applied to the pancreatic parenchyma Ba.

The detailed description above describes versions of a medical device representing examples of the inventive medical device disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of promoting adhesion between biological tissue comprising:
   disposing a medical device on a cut surface of one joint target site, wherein the one joint target site is a pancreatic parenchyma, the medical device comprising an adhesion promotion sheet including a first region that promotes adhesion of biological tissues and a second region provided outside the first region in a plane direction, and a pulling unit connected to the adhesion promotion sheet;
   pulling the pulling unit to deform the adhesion promotion sheet of the medical device to deform the second region;
   fixing the adhesion promotion sheet of the medical device to the one joint target site with a fixing member;
   interposing the adhesion promotion sheet between the one joint target and an other joint target site, wherein the other joint target site is a jejunum;
   joining the one joint target site and the other joint target site in a state where at least a portion of the adhesion promotion sheet is disposed between the pancreatic parenchyma and the jejunum; and
   indwelling the adhesion promotion sheet between the pancreatic parenchyma and the jejunum.

2. The method according to claim 1, wherein at least a portion of the connection section has a rigidity greater than a rigidity of the non-connection section.

3. The method according to claim 1, wherein the pulling unit includes a string-shaped member.

4. The method according to claim 1, wherein the pulling unit includes a strip-shaped member having a predetermined length, the strip-shaped member having a larger cross-sectional area than that of a string-shaped member.

5. The method according to claim 1, further comprising:
   adjusting an amount of deformation of the second region with an adjustment unit that limits the pulling operation of the pulling unit.

6. The method according to claim 1, wherein the second region includes a plurality of protruding portions disposed in a circumferential direction of the adhesion promotion sheet, and the method further comprises:
   inserting the pulling unit into a hole portion in each of the plurality of protruding portions.

7. A method of promoting adhesion between biological tissue comprising:
   disposing a medical device on a cut surface of one joint target site, the medical device comprising an adhesion promotion sheet including a first region that promotes adhesion of biological tissues, and a second region provided outside the first region in a plane direction, and a pulling unit connected to the adhesion promotion sheet,
   wherein the pulling unit includes a connection section connected to the second region and a non-connection section, the non-connection section is not connected to the second region and is configured to be pulled out of the adhesion promotion sheet, wherein the connection section of the pulling unit includes a first site having a rigidity higher than that of the non-connection section and a second site having a rigidity lower than that of the first site, and wherein the first site and the second site are alternately disposed along a circumferential direction of the adhesion promotion sheet;
   pulling the pulling unit to deform the adhesion promotion sheet of the medical device to deform the second region;
   fixing the adhesion promotion sheet of the medical device to the one joint target site;
   interposing the adhesion promotion sheet between the one joint target and an other joint target site;
   joining the one joint target site and the other joint target site in a state where at least a portion of the adhesion promotion sheet is disposed between the one joint target site and the other joint target site; and
   indwelling the adhesion promotion sheet between the one joint target site and the other joint target site.

8. The method according to claim 7, further comprising:
   connecting the connection to the second region with a length equal to or more than half the adhesion promotion sheet along a circumferential direction.

9. A method of promoting adhesion between biological tissue comprising:
   disposing a medical device on a cut surface of one joint target site, the medical device comprising an adhesion promotion sheet including a first region that promotes adhesion of biological tissues, wherein the first region is made of a biodegradable sheet having a plurality of through-holes that pass through the first region, and a second region provided outside the first region in a plane direction wherein the second region does not have any through-holes, and a pulling unit connected to the adhesion promotion sheet;
   pulling the pulling unit to deform the adhesion promotion sheet of the medical device to deform the second region;

fixing the adhesion promotion sheet of the medical device to the one joint target site;

interposing the adhesion promotion sheet between the one joint target and an other joint target site;

joining the one joint target site and the other joint target site in a state where at least a portion of the adhesion promotion sheet is disposed between the one joint target site and the other joint target site; and indwelling the adhesion promotion sheet between the one joint target site and the other joint target site.

* * * * *